US009207243B2

(12) United States Patent
Shanmugam et al.

(10) Patent No.: US 9,207,243 B2
(45) Date of Patent: Dec. 8, 2015

(54) USE OF GLUT4 INHIBITORS AND DNA DAMAGING AGENTS FOR TREATING MULTIPLE MYELOMA

(75) Inventors: Malathy Shanmugam, Lisle, IL (US); Samuel K. McBrayer, North Muskegon, MI (US); Steven T. Rosen, Evanston, IL (US)

(73) Assignee: Northwestern University, Evanston, IL (US)

( * ) Notice: Subject to any disclaimer, the term of this patent is extended or adjusted under 35 U.S.C. 154(b) by 800 days.

(21) Appl. No.: 13/435,625

(22) Filed: Mar. 30, 2012

(65) Prior Publication Data

US 2012/0252749 A1    Oct. 4, 2012

Related U.S. Application Data

(60) Provisional application No. 61/470,886, filed on Apr. 1, 2011.

(51) Int. Cl.
| | |
|---|---|
| *A01N 43/04* | (2006.01) |
| *A61K 31/70* | (2006.01) |
| *A01N 43/78* | (2006.01) |
| *A61K 31/425* | (2006.01) |
| *G01N 33/574* | (2006.01) |
| *A61K 31/427* | (2006.01) |
| *A61K 31/496* | (2006.01) |
| *A61K 31/69* | (2006.01) |
| *A61K 31/704* | (2006.01) |

(52) U.S. Cl.
CPC ........ *G01N 33/57484* (2013.01); *A61K 31/427* (2013.01); *A61K 31/496* (2013.01); *A61K 31/69* (2013.01); *A61K 31/704* (2013.01); *G01N 2800/52* (2013.01)

(58) Field of Classification Search
CPC .......................... A61K 31/427; A61K 31/704
USPC .................................................. 514/34, 365
See application file for complete search history.

(56) References Cited

PUBLICATIONS

McBrayer, S.K., Cheng, J.C., Singhai, S., Krett, N., Rosen, S.T., Shanmugam, M. (2012) Multiple myeloma exhibits novel dependence on GLUT4, GLUT8, and GLUT11: implications for glucose transporter-directed therapy. Blood, vol. 119, No. 20, p. 4686-4697.*
Kwon, O., Eck, P., Chen, S., Corpe, C.P., Lee, J.-H., Kruhlak, M., Levine, M. (2007) Inhibition of the intestinal glucose transporter GLUT2 by flavonoids. FASEB Journal, vol. 21, p. 366-377.*
Bazuine, M., van den Broek, P.J.A., Antonie Maassen, J. (2005) Genistein directly inhibits GLUT4-mediated glucose uptake in 3T3-L1 adipocytes. Biochemical and Biophysical Research Communications, vol. 326, p. 511-514.*
Wood, T.E., Dalili, S., Simpson, C.D., Hurren, R., Mao, X., Saiz, F.S., Gronda, M., Eberhard, Y., Minden, M.D., Bilan, P.J., Klip, A., Batey,
R.A., Schimmer, A.D. (2008) Molecular Cancer Therapy, vol. 7, No. 11, p. 3546-3555.*
Plosker, G.L. (2008) Pegylated Liposomal Doxorubicin. A Review of its Use in the Treatment of Relapsed or Refractory Multiple Myeloma. Drugs, vol. 68, No. 17, p. 2535-2551.*
"Combination Chemotherapy" by RnCeus® (2007) Retrieved [online] Feb. 26, 2015. Retrieved from <http://rnceus.com/chem/combo.html>.*
"Guidance for Industry: Food-Effect Bioavailability and Fed Bioequivalence Studies" (2002) Retrieved [online] Feb. 26, 2015. Retrieved from the internet <http://www.fda.gov/downloads/RegulatoryInformation/>.*
Airley et al., "Glucose transporter glut-1 expression correlates with tumor hypoxia and predicts metastasis-free survival in advanced carcinoma of the cervix", Clinical Cancer Research, 2001, 7(4): 928-934.
Augustin et al., "GLUT8 contains a [DE]XXXL[LI] sorting motif and localizes to a late endosomal/lysosomal compartment", Traffic, 2005, 6(12): 1196-1212.
Bartel et al., "F18-fluorodeoxyglucose positron emission tomography in the context of other imaging techniques and prognostic factors in multiple myeloma", Blood, 2009, 114(10): 2068-2076.
Berruti et al., "Time to progression in metastatic breast cancer patients treated with epirubicin is not improved by the addition of either cisplatin or lonidamine: final results of a phase III study with a factorial design", Journal of Clinical Oncology, 2002, 20(20): 4150-4159.
Bredell et al., "Value of FDG PET in the assessment of patients with multiple myeloma", American Journal of Roentgenology, 2005, 184(4): 1199-1204.
Cooper et al., "Glucose transporter-1 (GLUT-1): a potential marker of prognosis in rectal carcinoma?", British Journal of Cancer, 2003, 89(5): 870-876.
Dewan et al., "Efficient intervention of growth and infiltration of primary adult T-cell leukemia cells by an HIV protease inhibitor, ritonavir", Blood, 2006, 107(2): 716-724.
Doege et al., "Characterization of human glucose transporter (GLUT) 11 (encoded by SLC2A11), a novel sugar-transport facilitator specifically expressed in heart and skeletal muscle", Journal of Biological Chemistry, 2001, 359 (Pt 2): 443-449.
Doege et al., "GLUT8, a novel member of the sugar transport facilitator family with glucose transport activity" Journal of Biological Chemistry, 2000, 275(21): 16275-16280.
Durie et al., "Whole-body (18)F-FDG PET identifies high-risk myeloma", Journal of Nuclear Medicine, 2002, 43(11): 1457-1463.
Gandhi et al., "8-chloro-cAMP and 8-chloro-adenosine act by the same mechanism in multiple myeloma cells", Cancer Research, 2001, 61(14): 5474-5479.
Gills et al., "Nelfinavir, A lead HIV protease inhibitor, is a broad-spectrum, anticancer agent that induces endoplasmic reticulum stress, autophagy, and apoptosis in vitro and in vivo", Clinical Cancer Research, 2007, 13(17): 5183-5194.
Goldman et al., "GLUT1 and GLUT8 in endometrium and endometrial adenocarcinoma", Modern Pathology, 2006, 19(11): 1429-1436.
Gupta et al., "HIV protease inhibitors block Akt signaling and radiosensitize tumor cells both in vitro and in vivo", Cancer Research, 2005, 65(18): 8256-8265.

(Continued)

*Primary Examiner* — Scarlett Goon
(74) *Attorney, Agent, or Firm* — Andrus Intellectual Property Law, LLP

(57) ABSTRACT

Methods of treating cancer comprising administering inhibitors of glucose transporters (GLUTs) are provided. Methods of predicting whether a cancer will respond to treatment with a GLUT inhibitor also are provided.

2 Claims, 9 Drawing Sheets

(56) References Cited

PUBLICATIONS

Hertel et al., "A structural basis for the acute effects of HIV protease inhibitors on GLUT4 intrinsic activity", Journal of Biological Chemistry, 2004, 279(53): 55147-55152.

Hou et al., "Ins (endocytosis) and outs (exocytosis) of GLUT4 trafficking", Current Opinion in Cell Biology, 2007, 19(4): 466-473.

Hsu et al., "Multiple-dose pharmacokinetics of ritonavir in human immunodeficiency virus-infected subjects", Antimicrobial Agents and Chemotherapy, 1997, 41(5): 898-905.

Jin et al., "Metabolic catastrophe as a means to cancer cell death", Journal of Cell Science, 2007, 120 (Pt 3): 379-383.

Kalla Vyas et al., "Effects of the HIV protease inhibitor ritonavir in GLUT4 knockout mice", Journal of Biological Chemistry, 2010, 285(47): 36395-36400.

Koster et al., "HIV protease inhibitors acutely impair glucose-stimulated insulin release", Diabetes, 2003, 52(7): 1695-1700.

Kumar et al., "Ritonavir blocks AKT signaling, activates apoptosis and inhibits migration and invasion in ovarian cancer cells", Molecular Cancer, 2009, 8: 26.

Macheda et al.,"Molecular and cellular regulation of glucose transporter (GLUT) proteins in cancer", Journal of Cellular Physiology, 2005, 202(3): 654-662.

Manolescu et al., "Facilitated hexose transporters: new perspectives on form and function", Physiology, 2007, 22: 234-240.

Maschek et al., "2-deoxy-D-glucose increases the efficacy of adriamycin and paclitaxel in human osteosarcoma and non-small cell lung cancers in vivo", Cancer Research, 2004, 64(1): 31-34.

Murata et al., "The mechanism of insulin resistance caused by HIV protease inhibitor therapy", Journal of Biological Chemistry, 2000, 275(27): 20251-20254.

Noor et al., "Indinavir acutely inhibits insulin-stimulated glucose disposal in humans: a randomized, placebo-controlled study", AIDS, 2002, 16(5): F1-8.

Pelicano et al., "Glycolysis inhibition for anticancer treatment", Oncogene, 2006, 25(34): 4633-4646.

Ramanathan et al., "Direct control of mitochondrial function by mTOR", Proceedings of the National Academy of Sciences, U S A, 2009, 106(52): 22229-22232.

Rudich et al., "Indinavir uncovers different contributions of GLUT4 and GLUT1 towards glucose uptake in muscle and fat cells and tissues", Diabetologia, 2003, 46(5): 649-658.

Shanmugam et al., "Targeting glucose consumption and autophagy in myeloma with the novel nucleoside analogue 8-aminoadenosine", Journal of Biological Chemistry, 2009, 284(39): 26816-26830.

Snyder et al., "Nitric oxide induces cell death by regulating anti-apoptotic BCL-2 family members", PLoS One, 2009, 4(9): e7059.

Srirangam et al., "Effects of HIV protease inhibitor ritonavir on Akt-regulated cell proliferation in breast cancer", Clinical Cancer Research, 2006, 12(6): 1883-1896.

Widmer et al., "GLUT8 subcellular localization and absence of translocation to the plasma membrane in PC12 cells and hippocampal neurons", Endocrinology, 2005, 146(11): 4727-4736.

Wuilleme-Toumi et al., "Mcl-1 is overexpressed in multiple myeloma and associated with relapse and shorter survival", Leukemia, 2005, 19(7): 1248-1252.

Xu et al., "Synergistic effect of targeting mTOR by rapamycin and depleting ATP by inhibition of glycolysis in lymphoma and leukemia cells", Leukemia, 2005, 19(12): 2153-2158.

Xu et al., "Inhibition of glycolysis in cancer cells: a novel strategy to overcome drug resistance associated with mitochondrial respiratory defect and hypoxia", Cancer Research, 2005, 65(2): 613-621.

Zamora-Leon et al., "Expression of the fructose transporter GLUT5 in human breast cancer", Proceedings of the National Academy of Sciences, U S A, 1996, 93(5): 1847-1852.

Zhao et al., "Glycogen synthase kinase 3alpha and 3beta mediate a glucose-sensitive antiapoptotic signaling pathway to stabilize Mcl-1", Molecular and Cellular Biology, 2007, 27(12): 4328-4339.

Zhong et al., "The glycolytic inhibitor 2-deoxyglucose activates multiple prosurvival pathways through IGF1R", Journal of Biological Chemistry, 2009, 284(35): 23225-23233.

Zong et al., "Alkylating DNA damage stimulates a regulated form of necrotic cell death", Genes and Development, 2004, 18(11): 1272-1282.

Castellani et al., "The Prognostic Value of F-18 Fluorodeoxyglucose Bone Marrow Uptake in Patients with Recent Diagnosis of Multiple Myeloma", Clinical Nuclear Medicine, Jan. 2010, 35(1):1-5.

Chow et al., "Anti-HIV Drugs for Cancer Therapeutics: Back to the Future?", Lancet Oncology, 2009, 10:61-71.

Ghias et al., "8-Amino-Adenosine Induces Loss of Phosphorylation of p38 Mitogen-Activated Protein Kinase, Extracellular Signal-Regulated Kinase 1/2, and Akt Kinase: Role in Induction of Apoptosis in Multiple Myeloma", Molecular Cancer Therapeutics, Apr. 2005, 4(4):569-577.

Ikezoe et al., "HIV-1 Protease Inhibitor Induces Growth Arrest and Apoptosis of Human Multiple Myeloma Cells Via Inactivation of Signal Transducer and Activator of Transcription 3 and Extracellular Signal-Regulated Kinase 1/2", Molecular Cancer Therapeutics, 2004, 3:473-479.

Ko et al., "Advanced Cancers: Eradication in all Cases Using 3-Bromopyruvate Therapy to Deplete ATP", Biochemical and Biophysical Research Communications, 2004, 324(1):269-275.

Krett et al., "8-Amino-Adenosine is a Potential Therapeutic Agent for Multiple Myeloma", 2004, 3:1411-1420.

Li et al., "Discovery of Non-Glucoside SGLT2 Inhibitors", Bioorganic & Medicinal Chemistry Letters, 2011, 21:2472-2475.

Maratou et al., "Glucose Transporter Expression on the Plasma Membrane of Resting and Activated White Blood Cells", 2007, 37:282-290.

Murata et al., "Indinavir Inhibits the Glucose Transporter Isoform Glut4 at Physiologic Concentrations", AIDS, 2002, 16:859-863.

Pedersen et al., Mitochondrial Bound Type II Hexokinase: A Key Player in the Growth and Survival of Many Cancers and an Ideal Prospect for Therapeutic Intervention, Biochimica et Biophysica Acta, 2002, 1555:14-20.

Piroli et al., "Peripheral Glucose Administration Stimulates the Translocation of GLUT8 Glucose Transporter to the Endoplasmic Reticulum in the Rat Hippocampus", The Journal of Comparative Neurology, 2002, 452:103-114.

Raez et al., "Phase I Trial of Glycolitic Inhibition with 2-Deoxyglucose and Docetaxel for Patients with Solid Tumors", Proceedings of the American Association for Cancer Research, 2006, 47.

Rodriguez-Enriquez et al., "Kinetics of Transport and Phosphorylation of Glucose in Cancer Cells", Journal of Cellular Physiology, 2009, 221:552-559.

Scheepers et al., "Mouse GLUT8: Genomic Organization and Regulation of Expression in 3T3-L1 Adipocytes by Glucose", Biochemical and Biophysical Research Communications, 2001, 288:969-974.

Scheepers et al., "Characterization of the Human SLC2A11 (GLUT11) Gene: Alternative Promoter Usage, Function, Expression, and Subcellular Distribution of Three Isoforms, and Lack of Mouse Orthologue", Molecular Membrane Biology, Jul.-Aug. 2005, 22(4):339-351.

Hresko et al., "HIV Protease Inhibitors Act as Competitive Inhibitors of the Cytoplasmic Glucose Binding Site of GLUTs with Differing Affinities for GLUT1 and GLUT4", PLoS One, Sep. 2011, 6(9):e25237.

Noor et al., "The effects of HIV protease inhibitors atazanavir and lopinavir/ritonavir on insulin sensitivity in HIV-seronegative healthy adults", AIDS, 2004, 18(16):2137.

* cited by examiner

USE OF GLUT4 INHIBITORS AND DNA DAMAGING AGENTS FOR TREATING MULTIPLE MYELOMA

CROSS-REFERENCE TO RELATED APPLICATIONS

This application claims the benefit of priority under 35 U.S.C. §119(e) to U.S. provisional patent application No. 61/470,886, filed on Apr. 1, 2011, the content of which is incorporated herein by reference in its entirety.

STATEMENT REGARDING FEDERALLY SPONSORED RESEARCH OR DEVELOPMENT

This invention was made with government support under grant numbers U54 CA 119341 and R01 CA085919 awarded by the National Institutes of Health. The government has certain rights in the invention.

BACKGROUND

Multiple myeloma is a fatal plasma cell malignancy characterized by elevated glucose utilization, a common feature of many cancers. This enhanced rate of glucose utilization forms the basis for the clinical monitoring of myeloma using $^{18}$fluoro-deoxyglucose positron emission tomography (FDG-PET) (Durie, Waxman et al. 2002; Bredella, Steinbach et al. 2005; Bartel, Haessler et al. 2009; and Castellani, Carletto et al. 2010). While glucose entry has been used for diagnostic and prognostic purposes, glucose entry in cancer has not been targeted for therapeutic purposes. Furthermore, previous attempts to target the glycolytic pathway in cancer involving clinical trials of hexokinase inhibitors have not yielded successful treatment strategies.

SUMMARY

Disclosed herein are methods of treating, diagnosing, and prognosing GLUT-dependent cancers. In some embodiments, the methods comprise administering to a patient in need thereof a GLUT inhibitor. Suitable GLUT-dependent cancers may include a GLUT4-dependent cancer, a GLUT8-dependent cancer, and a GLUT11-dependent cancer. Suitable GLUT inhibitors may include a GLUT4 inhibitor, a GLUT8 inhibitor, and a GLUT11 inhibitor.

In some embodiments of the disclosed methods, the GLUT-dependent cancer is a GLUT4-dependent cancer, which may include multiple myeloma. In some embodiments, the GLUT inhibitor is a GLUT4 inhibitor, which may include ritonavir or indinavir.

In other embodiments of the disclosed methods, the GLUT-dependent cancer is a GLUT8-dependent cancer, which may include multiple myeloma. In some embodiments, the GLUT8-dependent cancer is multiple myeloma. In further embodiments of the disclosed methods, the GLUT-dependent cancer is a GLUT1'-dependent cancer, which may include multiple myeloma.

Optionally, the methods further comprise administering a DNA damaging agent. In some embodiments, the DNA damaging agent is selected from doxorubicin, daunorubicin, epirubicin, idarubicin, valrubicin, and mitoxantrone.

Optionally, the methods further comprise administering a proteasome inhibitor. In some embodiments, the proteasome inhibitor is selected from bortezomib, epigallocatechin-3-gallate, and salinosporamide A.

In some embodiments of the disclosed methods, the GLUT inhibitor is administered after the patient has fasted. For example, the GLUT inhibitor may be administered after the patient has fasted for at least 4 hours, at least 6 hours, or at least 12 hours.

Also disclosed herein are methods of prognosing GLUT-dependent cancers. In some embodiments, the methods of prognosing GLUT-dependent cancers include predicting whether a cancer patient will respond to treatment with a GLUT inhibitor. In some embodiments, the methods comprise detecting a GLUT in cancer cells from the patient, wherein an elevated level of the GLUT and/or a mislocalization of the GLUT indicates that the patient will respond to treatment with the GLUT inhibitor.

In some embodiments of the methods of predicting whether a cancer patient will respond to treatment with a GLUT inhibitor, the methods comprise detecting GLUT4 in cancer cells from the patient, which may include detecting GLUT4 mislocalization in the cancer cells such as detecting mislocalization of GLUT4 to the plasma membrane. In some embodiments, detecting mislocalization of GLUT4 indicates that the patient will respond to treatment with a GLUT4 inhibitor. In some embodiments, detecting mislocalization comprises detecting increased localization of GLUT4 to the plasma membrane of the cancer cells.

In other embodiments of the methods of predicting whether a cancer patient will respond to treatment with a GLUT inhibitor, the methods comprise detecting GLUT8 in cancer cells from the patient. In some embodiments, an elevated level of GLUT8 indicates that the patient will respond to treatment with a GLUT8 inhibitor.

In further embodiments of the methods of predicting whether a cancer patient will respond to treatment with a GLUT inhibitor, the methods comprise detecting GLUT11 in cancer cells from the patient. In some embodiments, an elevated level of GLUT11 indicates that the patient will respond to treatment with a GLUT11 inhibitor.

In some embodiments of the methods of predicting whether a cancer patient will respond to treatment with a GLUT inhibitor, the cancer cells are cancer cells of blood. Suitable cancer cells for the methods of predicting whether a cancer patient will respond to treatment with a GLUT inhibitor include multiple myeloma cells.

DETAILED DESCRIPTION

Definitions

Figure 1:
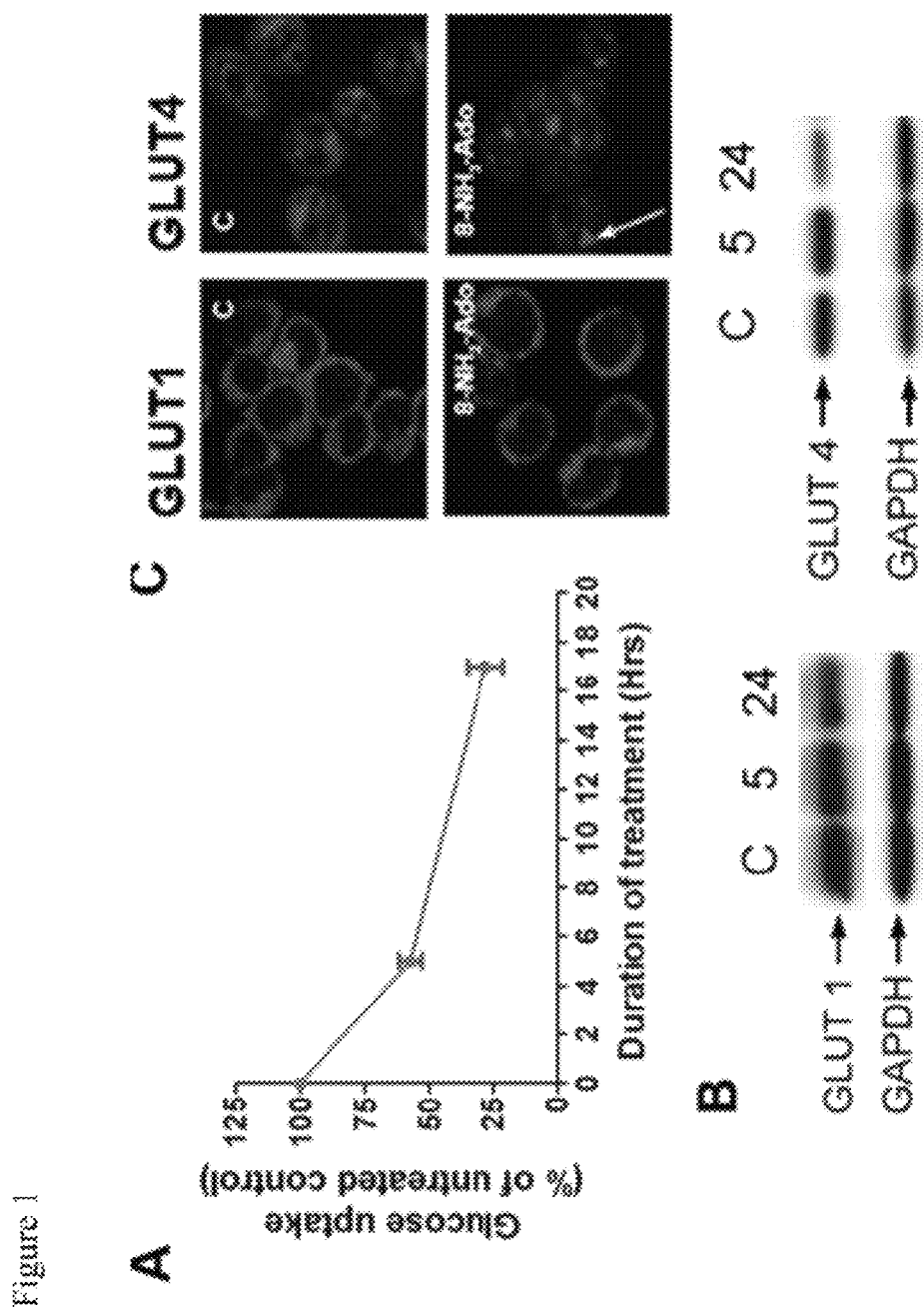
FIG. 1 shows that 8-NH2-Ado treatment induces GLUT4 translocation and an associated decline in glucose consumption in the sensitive MM.1S cell line. (A) Measurement of glucose consumed by MM.1S cells treated with 3 µM 8-NH2-Ado for 5 hours. Data are means±SEM (n=3). (B) MM.1S cells were treated for the indicated number of hours with 3 µM 8-NH2-Ado or not (C) prior to lysis and immunoblot analysis of GLUT1 and GLUT4 expression. (C) Immunostaining of GLUT1 and GLUT4 in MM.1S cells treated with 3 µM 8 NH2-Ado for 5 hours. Arrow indicates intracellular aggregation of GLUT4.

The subject matter disclosed herein is described using several definitions, as set forth below and throughout the application.

Unless otherwise noted, the terms used herein are to be understood according to conventional usage by those of ordinary skill in the relevant art. In addition to the definitions of terms provided below, it is to be understood that as used in the specification, embodiments, and in the claims, "a", "an", and "the" can mean one or more, depending upon the context in which it is used.

As used herein, "about," "approximately," "substantially," and "significantly" will be understood by persons of ordinary skill in the art and will vary to some extent on the context in which they are used. If there are uses of the term which are not clear to persons of ordinary skill in the art given the context in which it is used, "about" or "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising."

As used herein, the terms "patient" and "subject" may be used interchangeably and refer to one who receives medical care, attention or treatment. As used herein, the term is meant to encompass a person diagnosed with a disease such as cancer or at risk for developing cancer (e.g., a person who may be symptomatic for a cancer but who has not yet been diagnosed). A "patient in need thereof" may include a patient having, suspected of having, or at risk for developing a cell proliferative disorder or disease such as cancer, including multiple myeloma.

As used herein, the term "treatment," "treating," or "treat" refers to care by procedures or application that are intended to relieve illness or injury. Although it is preferred that treating a condition or disease such as multiple myeloma will result in an improvement of the condition, the term treating as used herein, does not indicate, imply, or require that the procedures or applications are at all successful in ameliorating symptoms associated with any particular condition. Treating a patient may result in adverse side effects or even a worsening of the condition which the treatment was intended to improve. Treating may include treating a patient having, suspected of having, or at risk for developing a cell proliferative disorder or disease such as cancer, including multiple myeloma.

As used herein the term "effective amount" refers to the amount or dose of the agent, upon single or multiple dose administration to the subject, which provides the desired effect in the subject under diagnosis or treatment. The disclosed methods may include administering an effective amount of the disclosed agents (e.g., as present in a pharmaceutical composition) for treating a cancer in the patient, whereby the effective amount slows the growth of, or reduces the size or extent of, the cancer.

An effective amount can be readily determined by the attending diagnostician, as one skilled in the art, by the use of known techniques and by observing results obtained under analogous circumstances. In determining the effective amount or dose of agent administered, a number of factors can be considered by the attending diagnostician, such as: the species of the patient; its size, age, and general health; the degree of involvement or the severity of the cancer; the response of the individual patient; the particular agent administered; the mode of administration; the bioavailability characteristics of the preparation administered; the dose regimen selected; the use of concomitant medication; and other relevant circumstances.

As used herein, the term "GLUT-dependent cancer" refers to a cancer in which there is an elevated level of at least one GLUT protein, mRNA, or pre-mRNA in at least some of the cancer cells, and/or in which at least one GLUT protein is mislocalized in at least some of the cancer cells. In some embodiments, there is an elevated level of at least one GLUT protein, mRNA, or pre-mRNA in at least 30%, at least 50%, or at least 75% of the cancer cells in a sample of cancer cells from the patient. In some embodiments, at least one GLUT protein is mislocalized in at least 30%, at least 50%, or at least 75% of the cancer cells in a sample of cancer cells from the patient. GLUT-dependent cancers include, but are not limited to, GLUT4-dependent cancers, GLUT8-dependent cancers, and GLUT11-dependent cancers. A particular GLUT-dependent cancer may be classified as more than one of a GLUT4-dependent cancer, a GLUT8-dependent cancer, a GLUT1'-dependent cancer, etc. Multiple myeloma is a nonlimiting exemplary GLUT4-dependent cancer. Multiple myeloma is also a nonlimiting exemplary GLUT8-dependent cancer, and a nonlimiting exemplary GLUT1'-dependent cancer.

As used herein, the term "GLUT inhibitor" refers to an agent that inhibits the activity of a GLUT protein, for example by direct inhibition of the protein, or by inhibition of expression of the protein. GLUT inhibitors include, but are not limited to, GLUT4 inhibitors, GLUT8 inhibitors, and GLUT11 inhibitors. Nonlimiting exemplary GLUT4 inhibitors include ritonavir, indinavir, and pharmaceutically acceptable salts thereof.

GLUT inhibitors may include analogs or derivatives of ritonavir, which may include "similar compounds as defined in the National Center for Biotechnology Information's PubChem database, such as compounds identified by the compound identification numbers (CID's): CID: 392622; CID: 16760215; CID: 10395099; CID: 9853294; CID: 60954; CID: 5076; CID: 44371188; CID: 44371171; CID: 44371165; CID: 44371081; CID: 44371069; CID: 44371023; CID: 44371021; CID: 44371020; CID: 44371019; CID: 44371018; CID: 44370991; CID: 22878492; CID: 22868003; CID: 22863118; CID: 22863027; CID: 22863019; CID: 22862950; CID: 22862923; CID: 19432988; CID: 18759200; CID: 18759116; CID: 18759083; CID: 18759081; CID: 18759065; CID: 18759050; CID: 18759039; CID: 18758899; CID: 18758893; CID: 18758866; CID: 18758863; CID: 18758854; CID: 18624597; CID: 515847; CID: 515824; CID: 515823; CID: 515818; CID: 515817; CID: 515815; CID: 482962; CID: 482960; CID: 482957; CID: 482956; CID: 482948; CID: 482947; CID: 482944; CID: 482943; CID: 49823250; CID: 44371241; CID: 44371229; CID: 44371228; CID: 4437.1227; CID: 44371170; CID: 44371169; CID: 44371108; CID: 44370961; CID: 44370960; CID: 44370959; CID: 44370896; CID: 44370895; CID: 44370881; CID: 44334979; CID: 22878493; CID: 22867769; CID: 22865244; CID: 22863127; CID: 22863125; CID: 22863035; CID: 22863031; CID: 22863015; CID: 22863014; CID: 22863010; CID: 22862997; CID: 22862993; CID: 22862986; CID: 22862979; CID: 22862969; CID: 22862946; CID: 22862939; CID: 22862927; CID: 22862919; CID: 22862904; CID: 22862857; CID: 22862838; CID: 22862827; CID:

22862817; CID: 18759212; CID: 18759181; and CID: 18759178; which entries are incorporated herein by reference in their entireties.

GLUT inhibitors may include analogs or derivatives of idinavir, which may include "similar compounds" as defined in the National Center for Biotechnology Information's PubChem database, such as compounds identified by the compound identification numbers (CID's): CID: 5362440; CID: 46930980; CID: 23351650; CID: 23351649; CID: 11399365; CID: 9830402; CID: 9830401; CID: 3033831; CID: 60944; CID: 3706; CID: 51346630; CID: 23232405; CID: 44629557; CID: 24848178; CID: 5496641; CID: 5495865; CID: 5495864; CID: 5493607; CID: 5484730; CID: 3400922; CID: 508523; CID: 508522; CID: 496986; CID: 446635; CID: 104877; CID: 44366310; CID: 44343215; CID: 20870851; CID: 18477694; CID: 16639401; CID: 16639395; CID: 5479510; CID: 455962; CID: 44366356; CID: 44366297; CID: 44342144; CID: 23375344; CID: 20979070; CID: 18730500; CID: 10974220; CID: 10941221; CID: 10908345; CID: 9853161; CID: 5496583; CID: 5481985; CID: 489318; CID: 480986; CID: 446133; CID: 49757450; CID: 46930979; CID: 44628479; CID: 44366619; CID: 44366414; CID: 44366309; CID: 44342037; CID: 44326584; CID: 23377516; CID: 23375501; CID: 20846145; CID: 11954281; CID: 9874011; CID: 5481045; CID: 5481043; CID: 5462355; CID: 469114; CID: 469111; CID: 394079; CID: 60958; CID: 44563986; CID: 44563984; CID: 44367246; CID: 44366592; CID: 44366576; CID: 25015662; CID: 24970688; CID: 24892955; CID: 24892954; CID: 23351700; CID: 23315005; CID: 23305628; CID: 22489378; CID: 21576401; CID: 21147539; CID: 20842172; CID: 18002348; CID: 9988227; CID: 9940047; CID: 9832401; CID: 6475670; CID: 5481046; CID: 5481044; CID: 5464652; CID: 493833; CID: 479179; CID: 479178; CID: 479168; CID: 469115; CID: 469112; CID: 44366295; and CID: 44342145; which entries are incorporated herein by reference in their entireties.

As used herein, the term "DNA damaging agent" refers to a therapeutic agent that damages replicating DNA. In some embodiments, a DNA damaging agent damages cancer cell DNA. In some embodiments, a DNA damaging agent is used to treat cancer, for example, in combination with a GLUT inhibitor, as described herein. Nonlimiting exemplary DNA damaging agents include, but are not limited to, doxorubicin, daunorubicin, epirubicin, idarubicin, valrubicin, and mitoxantrone.

As used herein, the term "fasted" indicates that a patient has not taken in, by mouth, feeding tube, intravenously, or other route, a substance containing glucose for a certain length of time. When a patient has only eliminated glucose for a certain length of time, the fast may be referred to herein as a "glucose fast". In some embodiments, a fasting patient has not taken in a substance containing calories (referred to herein as a "caloric fast"). In some embodiments, a fasting patient has not taken in any substances except water (referred to herein as a "complete fast"). In some embodiments, a fasting patient has not taken in any substances, including water (referred to herein as a "complete fast without water").

The term "proteasome inhibitor" as used herein refers to an agent that blocks the action of proteasomes, which are cellular complexes that break down proteins. In some embodiments, a proteasome inhibitor is used to treat cancer, for example, in combination with a GLUT inhibitor, as described herein. Suitable proteasome inhibitors for use in the methods disclosed herein may include but are not limited to peptide boronic acid compounds, NPI-0052 (salinosporamide A analogs), 2-pyrrolidone compounds, epigallocatechin 3-gallate (EGCG) analogs (in particular those analogs that are specific for proteasome inhibition), PR-171, epoxomycin analogs, peptide analogs, tetrapeptide derivatives, tyropeptide A analogs, and combinations thereof. In some embodiments, the proteasome inhibitor inhibits one or more enzymatic activities of a proteasome selected from $\beta 1$ subunit activity (chymotryptic-like activity), $\beta 2$ subunit activity (tryptic-like activity), and $\beta 5$ subunit activity (post-glutamyl peptidyl hydrolytic-like activity). One suitable proteasome inhibitor is bortezomib (BZ) or a pharmaceutically acceptable salt thereof, which for example, may be administered to a patient at a dosage of about of about 0.7 mg/m$^2$ to about 1.9 mg/m$^2$. Preferably, the proteasome inhibitor selectively inhibits proteasome activity. Nonlimiting exemplary proteasome inhibitors include bortezomib, disulfiram, epigallocatechin-3-gallate, and salinosporamide A.

The term "mislocalization" as used herein refers to a difference in the intracellular localization of a protein in a cancer cell relative to the localization of the protein in a control cell of similar type. For example, a protein is considered mislocalized if it is located throughout the cytoplasm in a control cell, but is present more predominantly at the cell membrane in a cancer cell (compared to the control cell), whether or not the protein is also located throughout the cytoplasm in the cancer cell. Nonlimiting exemplary control cells for a multiple myeloma are normal B lymphocytes.

A biological molecule is considered to be present at an "elevated level," as used herein, when the biological molecule is present as levels that are at least 20% greater in a cancer cell than in a control cell of similar type. Biological molecules include, but are not limited to, proteins, pre-mRNA, and mRNA.

In some embodiments of the disclosed methods of treating cancer, the methods include administering a GLUT inhibitor. In some such embodiments of the methods of treating cancer, the cancer is a GLUT-dependent cancer. Non-limiting exemplary GLUT-dependent cancers include multiple myeloma. A multiple myeloma may be a GLUT4-dependent, GLUT8-dependent, and/or a GLUT11-dependent cancer.

In some embodiments of the disclosed methods of treating cancer, the cancer is treated with a GLUT4 inhibitor. Suitable cancers for treatment in these include multiple myeloma. Non-limiting exemplary GLUT4 inhibitors include the protease inhibitors ritonavir, indinavir, analogs, derivatives, and pharmaceutically acceptable salts thereof. In some embodiments, GLUT4 is mislocalized in multiple myeloma cells. Typically, GLUT4 is located in the cytoplasm, and localizes to the plasma membrane in an insulin-dependent manner. In multiple myeloma cells, in some embodiments, GLUT4 accumulates at the plasma membrane in the absence of insulin. Accordingly, in some embodiments, a GLUT4 inhibitor can be used to target multiple myeloma cells specifically by administering the GLUT4 inhibitor under fasting conditions, such that GLUT4 is not plasma membrane-localized in normal cells in which GLUT4 localization is insulin-responsive. In various embodiments, the fasting conditions are glucose fasting conditions, caloric fasting conditions, complete fasting conditions, or complete fasting conditions without water. In some embodiments, the patient has fasted for at least 2, at least 4, at least 6, at least 8, or at least 12 hours before administration of the GLUT4 inhibitor.

In some embodiments of the disclosed methods of treating cancer, the cancer is treated with a GLUT8 inhibitor. Suitable cancers for treatment in these include multiple myeloma. In some embodiments, GLUT8 is present at higher levels, at the protein and/or mRNA level, in multiple myeloma cells. Thus, in some embodiments, a GLUT8-dependent cancer may be more sensitive to a GLUT8 inhibitor than normal cells.

In some embodiments of the disclosed methods of treating cancer, the cancer is treated with a GLUT11 inhibitor. Suitable cancers for treatment in these include multiple myeloma. In some embodiments, GLUT11 is present at higher levels, at the protein and/or mRNA level, in multiple myeloma cells. Thus, in some embodiments, a GLUT11-dependent cancer may be more sensitive to a GLUT11 inhibitor than normal cells.

In some embodiments of the disclosed methods of treating cancer, a GLUT-dependent cancer is treated with a combination therapy comprising a GLUT inhibitor and one or more additional therapeutic molecules. In some embodiments, a GLUT-dependent cancer is treated with the combination of a GLUT inhibitor and a DNA damaging agent. In some such embodiments, the cancer is a GLUT4-dependent cancer and the GLUT inhibitor is a GLUT4 inhibitor. Thus, in some embodiments, a GLUT4-dependent cancer is treated with the combination of a GLUT4 inhibitor and a DNA damaging agent. Non-limiting exemplary DNA damaging agents include doxorubicin, daunorubicin, epirubicin, idarubicin, valrubicin, and mitoxantrone. In some embodiments, a GLUT4-dependent cancer is treated with the combination of a GLUT4 inhibitor and doxorubicin. In some embodiments, a GLUT4-dependent cancer is treated with the combination of ritonavir and/or indinavir, and doxorubicin. In some embodiments, multiple myeloma is treated with a combination of ritonavir and/or indinavir, and doxorubicin.

In some embodiments of the disclosed methods of treating cancer, a GLUT-dependent cancer is treated with the combination of a GLUT inhibitor and a proteasome inhibitor. In some such embodiments, the cancer is a GLUT8-dependent cancer and the GLUT inhibitor is a GLUT8 inhibitor. Non-limiting exemplary proteasome inhibitors include bortezomib, disulfiram, epigallocatechin-3-gallate, and salinosporamide A. In some embodiments, a cancer is treated with the combination of a GLUT8 inhibitor and bortezomib.

In some embodiments of the disclosed methods of prognosing cancer, methods of predicting whether a cancer patient will respond to treatment with a GLUT inhibitor are provided. In some such embodiments, the method comprises detecting the level of a GLUT protein, mRNA, and/or pre-mRNA in the cancer cells. The level of a GLUT protein, mRNA, and/or pre-mRNA can be determined by any method. Many such methods are known in the art, and one skilled in the art can select a suitable method for determining the level of a particular protein, mRNA, and/or pre-mRNA in a cell. In some embodiments, the level of the protein, mRNA, and/or pre-mRNA in the cancer cell is compared to the level of the same protein, mRNA, and/or pre-mRNA in a control cell or normal cell. In some embodiments, the level of a GLUT protein, mRNA, and/or pre-mRNA in the cancer cell is compared to the level of a control protein, mRNA, and/or pre-mRNA in the cancer cell, wherein the normal ratio of the level of the control protein, mRNA and/or pre-mRNA to the GLUT protein, mRNA and/or pre-mRNA is known. In some embodiments, if the level of GLUT4, GLUT8, or GLUT11 is elevated in the cancer cell, the cancer is predicted to respond to an inhibitor of GLUT4, GLUT8, or GLUT11.

In some embodiments of the disclosed methods of prognosing cancer, the method comprises detecting mislocalization of a GLUT protein in the cancer cells. In some such embodiments, detecting mislocalization of a GLUT protein indicates that a cancer will respond to a GLUT inhibitor. Mislocalization is any difference in the localization of a GLUT protein in a cancer cell relative to a control or normal cell of a similar type. A "similar type" or normal cell includes, for example, the cell type from which the cancer is derived. As a non-limiting example, a normal cell to which a multiple myeloma can be compared is a B lymphocyte. In some embodiments, a difference in the localization of a GLUT protein includes situations in which the GLUT protein is found in all of the same locations as it is found in the normal cell, but at different levels at those locations relative to one another. Thus, for example, if a GLUT protein is localized evenly throughout the cytoplasm in a normal cell, in some embodiments, the GLUT protein is mislocalized in a cancer cell if it is localized evenly throughout the cytoplasm, but is also present at the plasma membrane in higher levels than in the cytoplasm generally, unlike in the normal cell. See, e.g., FIG. 3. As a non-limiting example, mislocalization of GLUT4 to the plasma membrane in multiple myeloma cells indicates that the multiple myeloma will respond to a GLUT4 inhibitor.

Illustrative Embodiments

The following embodiments are illustrative and are not intended to limit the disclosed subject matter.

Embodiment 1. A method of treating a GLUT-dependent cancer in a patient comprising administering a GLUT inhibitor.

Embodiment 2. The method of embodiment 1, wherein the GLUT-dependent cancer is selected from a GLUT4-dependent cancer, a GLUT8-dependent cancer, and a GLUT11-dependent cancer.

Embodiment 3. The method of embodiment 2, wherein the GLUT inhibitor is selected from a GLUT4 inhibitor, a GLUT8 inhibitor, and a GLUT11 inhibitor.

Embodiment 4. The method of embodiment 2, wherein the GLUT dependent cancer is a GLUT4-dependent cancer.

Embodiment 5. The method of embodiment 3, wherein the GLUT4-dependent cancer is multiple myeloma.

Embodiment 6. The method of embodiment 4 or embodiment 5, wherein the GLUT inhibitor is a GLUT4 inhibitor.

Embodiment 7. The method of embodiment 6, wherein the GLUT4 inhibitor is selected from ritonavir and indinavir.

Embodiment 8. The method of embodiment 7, wherein the GLUT4 inhibitor is ritonavir.

Embodiment 9. The method of embodiment 2, wherein the GLUT-dependent cancer is a GLUT8-dependent cancer.

Embodiment 10. The method of embodiment 9, wherein the GLUT8-dependent cancer is multiple myeloma.

Embodiment 11. The method of embodiment 2, wherein the GLUT-dependent cancer is a GLUT11-dependent cancer.

Embodiment 12. The method of embodiment 11, wherein the GLUT11-dependent cancer is multiple myeloma.

Embodiment 13. The method of any one of the preceding embodiments, wherein the method further comprises administering a DNA damaging agent.

Embodiment 14. The method of embodiment 13, wherein the DNA damaging agent is selected from doxorubicin, daunorubicin, epirubicin, idarubicin, valrubicin, and mitoxantrone.

Embodiment 15. The method of embodiment 14, wherein the DNA damaging agent is doxorubicin.

Embodiment 16. The method of any one of the preceding embodiments, wherein the method further comprises administering a proteasome inhibitor.

Embodiment 17. The method of embodiment 16, wherein the proteasome inhibitor is selected from bortezomib, disulfiram, epigallocatechin-3-gallate, and salinosporamide A.

Embodiment 18. The method of embodiment 17, wherein the proteasome inhibitor is bortezomib.

Embodiment 19. The method of any one of the preceding embodiments, wherein the GLUT inhibitor is administered after the patient has fasted for at least 4 hours.

Embodiment 20. The method of embodiment 19, wherein the GLUT inhibitor is administered after the patient has fasted for at least 6 hours.

Embodiment 21. The method of embodiment 20, wherein the GLUT inhibitor is administered after the patient has fasted for at least 12 hours.

Embodiment 22. A method of predicting whether a cancer patient will respond to treatment with a GLUT inhibitor, comprising detecting a GLUT in cancer cells from the patient, wherein an elevated level of the GLUT or a mislocalization of the GLUT indicates that the patient will respond to treatment with the GLUT inhibitor.

Embodiment 23. The method of embodiment 22, wherein GLUT4 is detected in cancer cells from the patient.

Embodiment 24. The method of embodiment 23, wherein mislocalization of GLUT4 indicates that the patient will respond to treatment with a GLUT4 inhibitor.

Embodiment 25. The method of embodiment 24, wherein the mislocalization comprises increased localization of GLUT4 to the plasma membrane of the cancer cells.

Embodiment 26. The method of embodiment 22, wherein GLUT8 is detected in cancer cells from the patient.

Embodiment 27. The method of embodiment 26, wherein an elevated level of GLUT8 indicates that the patient will respond to treatment with a GLUT8 inhibitor.

Embodiment 28. The method of embodiment 22, wherein GLUT11 is detected in cancer cells from the patient.

Embodiment 29. The method of embodiment 24, wherein an elevated level of GLUT11 indicates that the patient will respond to treatment with a GLUT11 inhibitor.

Embodiment 30. The method of any one of embodiment 22 to 29, wherein the cancer cells are multiple myeloma cells.

EXAMPLES

The following examples are illustrative and are not intended to limit the disclosed subject matter.

Brief Summary

We have identified a unique means to target aerobic glycolysis in multiple myeloma via inhibition of specific glucose transporters (GLUTs), leading to acute inhibition of all glucose-dependent cellular processes in a more selective and potent manner than has previously been achieved. This improved potency may be attributable to the over-riding flux control associated with trans-plasma membrane glucose movement mediated by specific glucose transporters, relative to that of glucose phosphorylation by hexokinase in tumor cells, a scenario which has previously been demonstrated (Rodriguez-Enriquez, Marin-Hernandez et al. 2009). While some analyses of GLUT gene family expression patterns have been performed in specific cancer types, the functional contributions of individual isoforms to the tumor cell metabolic phenotype have not been clarified or investigated. It is a widely held view in the field that increased GLUT1 expression primarily accounts for increased glucose transport rates in cancer. In contrast, our unbiased studies of GLUT expression and function demonstrate that myeloma cells are highly reliant upon GLUT4 to support elevated, basal glucose consumption. We observe slightly increased protein levels of GLUT4 in myeloma cell lines as well as a widespread mislocalization of GLUT4 to the plasma membrane. These alterations are critical for sustaining the metabolic homeostasis, proliferation, and survival of myeloma cells. We have also demonstrated that suppressing GLUT4 leads to significant suppression of Mcl-1, a pro-survival regulator of apoptosis known to play a key role in sustaining hematologic cancer cell survival and chemoresistance.

Therefore, therapeutic inhibition of GLUT4 constitutes a novel strategy to compromise the metabolism and survival of myeloma cells and induce tumor regression in MM patients. This approach represents a promising advancement in our ability to target the glycolytic phenotype of cancer cells and could yield superior patient outcomes relative to the minimal efficacy of hexokinase inhibitor administration. As a means of achieving this goal, we have identified an FDA approved HIV protease inhibitor, ritonavir, which has been demonstrated to elicit a selective, off-target inhibitory effect on GLUT4 in vivo. Treatment of myeloma cell lines and patient samples with ritonavir recapitulates the effects of GLUT4 knockdown, including reduced glucose consumption, viability, and proliferation. Ritonavir exposure also sensitizes myeloma cell lines to the DNA damaging therapeutic doxorubicin, an effect associated with other glycolysis inhibition strategies as well. The efficacy of ritonavir is proof-of-principle that compounds targeting GLUT4 can be successfully administered to humans, and thus can be expected to be used safely for the treatment of GLUT4-dependent cancers. Our discovery provides rationale for the development of more potent inhibitors of GLUT4, potentially derived from ritonavir, and for the combination of these molecules with DNA damaging agents (such as doxorubicin) for cancer treatment. In addition to our discovery of GLUT4 de-regulation in MM, our studies reveal widespread overexpression of GLUT8 and GLUT11 in myeloma cell lines. Both GLUT8 and GLUT11 activities are necessary for proliferation of myeloma cells: hence, these proteins may represent targets with substantial therapeutic windows due to their extremely limited distribution profiles in normal tissues. The development of small molecule or biological inhibitors of GLUT8 and GLUT11 may yield highly myeloma-specific treatment approaches which circumvent the ubiquitous, dose-limiting toxicities associated with many traditional chemotherapeutics.

Background

The movement of glucose across cellular membranes is carried out by a 14 member family of ATP-independent facilitative transporters (GLUTs), each with unique tissue-specific expression, subcellular localization, substrate utilization, kinetics and function (Manolescu, Witkowska et al. 2007) which are grouped into 3 subclasses. Class I includes GLUTs 1-4 and GLUT14, thought to be a gene duplication of GLUT3. Class II consists of GLUTs 5, 7, 9 and 11 which exhibit widely varying affinities for glucose and more limited tissue distribution profiles in comparison to Class I transporters, suggesting distinct metabolic roles. Class III consists of GLUTs 6, 8, 10, 12 and 13, with 8 and 10 demonstrating high affinities for glucose and GLUT13 being a myo-inositol transporter. In normal human B cells, GLUTs 1, 3 and 4 play a role in glucose transport (Maratou, Dimitriadis et al. 2007). The overexpression of GLUTs is increasingly recognized as a prognostic factor in various cancers. GLUT1 has been implicated in hepatic, pancreatic, breast, esophageal, brain, renal, lung, cutaneous, colorectal, endometrial, ovarian and renal cancers (Airley, Loncaster et al. 2001; Cooper, Sarioglu et al. 2003; Macheda, Rogers et al. 2005), GLUT12 overexpression in breast and prostate cancer (Macheda, Rogers et al. 2005), GLUT5 overexpression in breast cancer cell lines (Zamora-Leon, Golde et al. 1996) and GLUT8 in endometrial adenocarcinoma (Goldman, Katz et al. 2006). Glucose transport across the plasma membrane into the cell is a critical rate limiting step preceding all downstream glucose-dependent metabolic pathways. A recent analysis of the catalytic efficiencies of GLUTs and hexokinase in rat adenocarcinoma and HeLa cervical carcinoma cells demonstrated that the low $V_{max}$/high $K_m$ values for GLUTs in comparison to hexokinase proved it to be the rate limiting step in glycolysis (Rodriguez-Enriquez, Marin-Hernandez et al. 2009) and therefore a more suitable target than other distal glycolytic enzymes such as hexokinase that also regulate flux through the pathway.

Various in vitro studies have demonstrated the utility of targeting glycolysis as a mode of sensitizing cancer cells to various treatments, including DNA damaging agents, radiation therapy and mTOR inhibitors. Current drug development strategies targeting glycolysis have largely focused on hexokinase inhibitors (Pedersen, Mathupala et al. 2002) such as 2DG, 3-bromopyruvate and lonidamine (Ko, Smith et al. 2004; Pelicano, Martin et al. 2006; Jin, DiPaola et al. 2007). 2DG has been shown to sensitize various cancers to therapeutics such as doxorubicin and paclitaxel (Maschek, Savaraj et al. 2004). However, 2DG activates AKT and IGFIR signaling, eliciting several pro-tumorigenic off-target effects (Zhong, Xiong et al. 2009) in addition to promoting chemo-resistance through induction of p-glycoprotein (Pelicano, Martin et al. 2006). The clinical drawbacks of these compounds include potential toxicity to other glucose-utilizing tissues, high concentrations required for efficacy and low stability of 3-bromopyruvate in solution (Xu, Pelicano et al. 2005), thus highlighting the need for newer approaches to target abnormal glucose utilization in cancer. Indeed, clinical trials involving these compounds have generated few positive outcomes. A phase I trial combining 2DG and docetaxel resulted in only six cases of disease stabilization and one partial response out of an evaluable pool of 18 patients (Raez LE 2006). The lack of efficacy reported may be related to the inability to dose more aggressively since Grade 3 hyperglycemia was noted to have occurred in multiple patients. The systemic metabolic perturbations induced by 2DG may prohibit its use at dosages required to elicit the antitumor effects observed in both murine and in vitro cancer models. In the case of lonidamine, a recent phase III study in previously untreated breast cancer patients demonstrated a 9% increase in overall response rate in the patient cohort receiving epirubicin plus lonidamine in comparison to the cohort receiving epirubicin alone (Berruti, Bitossi et al. 2002). This slight improvement in patient outcome bordered on but did not reach statistical significance. Clinical investigations of 3-bromopyruvate have yet to commence.

The lack of progress in targeting cancer-associated aerobic glycolysis via hexokinase inhibition warrants the development of alternative approaches. The concept of targeting glycolysis through GLUT4 inhibition improves upon the hexokinase-directed strategies by conferring additional selectivity for tumor versus nonmalignant tissue. While hexokinase is expressed in virtually all cell types, GLUT4 expression is largely confined to myocytes and adipocytes. The restricted expression of GLUT4 to muscle and fat tissues reduces the risk of encountering dose-limiting toxicities with a targeting agent relative to a ubiquitously expressed target such as hexokinase. Furthermore, GLUT4 is not constitutively active in these normal cell types; its activity is tightly regulated by systemic insulin levels via intracellular sequestration. However, in MM cells we detect a substantial fraction of total GLUT4 protein exhibiting cell surface localization under low-insulin conditions. Therefore, if chemical or biological inhibitors of GLUT4 were administered to MM patients during normal physiological periods of diminished plasma insulin concentrations (i.e. after fasting or during sleep), these therapeutics would be expected to exhibit maximal tumor selectivity under these conditions. This scenario should facilitate aggressive dosing options for GLUT4 inhibitors and translate to more potent target inhibition.

To realize this goal, we have tested the HIV protease inhibitor ritonavir in cell culture myeloma models due to a specific, off-target inhibitory effect of this drug on GLUT4 which has been documented in a number of publications. The HIV PI (protease inhibitors), FDA approved since the early 1990s, are highly effective in suppressing viral replication and improving patient outcome by targeting HIV-encoded aspartyl protease (Chow, Jiang et al. 2009). However, patients eventually develop diabetic symptoms consistent with an inhibition of peripheral glucose consumption. Several in vitro and in vivo studies have identified GLUT4 to be the molecular target of this class of drugs. Altered glucose homeostasis observed in these patients is thought to be due to non-covalent binding of the PI to a unique structural domain within GLUT4. In vitro studies have demonstrated the selectivity of these compounds for GLUT4 in comparison to GLUTs 1, 2, 3, and 8 and have established $IC_{50}$ values for GLUT4 within the range of physiological concentrations (Murata, Hruz et al. 2002; Rudich, Konrad et al. 2003). Studies in primary rat adipocytes indicated a reversible non-competitive mode of GLUT4 inhibition with clinically achievable concentrations of indinavir (i.e. $K_i$ of 15 uM) (Murata, Hruz et al. 2000; Murata, Hruz et al. 2002). Indinavir was demonstrated to inhibit labeling of GLUT4 with a GLUT4 specific peptide, further supporting a direct interaction (Hertel, Struthers et al. 2004). Treatments with doses of insulin that lead to GLUT4 (but not GLUT') plasma membrane translocation increase the efficiency of glucose transport inhibition by indinavir (Rudich, Konrad et al. 2003). However, indinavir does not alter GLUT4 localization or glucokinase activity, again suggesting direct inhibition of transporter activity as the mechanism underlying impairment of glucose uptake (Koster, Remedi et al. 2003; Rudich, Konrad et al. 2003). These effects are presumed to occur independently of changes in GLUT4 expression due to the short time course required to elicit this response (i.e. seconds to minutes) (Rudich, Konrad et al. 2003; Hertel, Struthers et al. 2004). Indinavir is most extensively characterized for its GLUT4 inhibitory properties within this class of drugs and is associated with a high risk of developing diabetes (Noor, Seneviratne et al. 2002).

HIV PIs have previously been considered as cancer therapeutics primarily due to their success in treating HIV-related Kaposi's sarcoma (Chow, Jiang et al. 2009). PI have demonstrated efficacy against breast (Srirangam, Mitra et al. 2006), ovarian (Kumar, Bryant et al. 2009), adult T cell leukemia (Dewan, Uchihara et al. 2006) and non-small cell lung carcinoma (Gills, Lopiccolo et al. 2007) in both in vitro and in vivo studies and are currently being tested in clinical trials, however not based on their glucose modulatory properties. One recent study showed growth inhibitory and/or apoptotic effects of ritonavir in two myeloma cell lines and one lymphoblastoid cell line (Ikezoe, Saito et al. 2004). These effects were correlated to inhibition of STAT3 and ERK activities. While this study reaffirms the utility of PI in myeloma, an investigation of greater depth is required to confirm the mechanism of action and justify use in myeloma. PI are known to differentially impact Akt, NFκB, ER stress, cyclin dependent kinase activity and pRb levels in a cell type-specific manner, (Srirangam, Mitra et al. 2006; Kumar, Bryant et al. 2009) potentially contributing to the observed toxicity. In a study comparing various PI for radio-sensitizing properties in tumor cells with mutations in EGFR, H-Ras or K-Ras, ritonavir and indinavir were less potent compared to other compounds. The inability of ritonavir and indinavir to sensitize these tumor cells to radiation therapy was attributed to an inability to inactivate Akt (Gupta, Cerniglia et al. 2005). Therefore the effects of an individual PI are clearly cell type specific. No PI has been investigated in a cancer model or clinical trial based on their ability to inhibit GLUT4-mediated glucose transport. Based on our in vitro studies, we believe HIV PI could be used as stand-alone monotherapies or in combinatorial treatment regimens to synergize with therapeutics like rapamycin or DNA damaging agents whose activities are known to be potentiated upon inhibition of glycolysis (long, Ditsworth et al. 2004; Xu, Pelicano et al. 2005; Ramanathan and Schreiber 2009).

Upon uncovering such a prominent role for GLUT4 in myeloma, our investigation into the connection between GLUT4-dependent glucose uptake and MM cell survival delineates a pathway linking GLUT4 activity with the maintenance of Mcl-1 protein expression. The ability to substantially reduce Mcl-1 expression through GLUT4 inhibition has profound clinical implications due to the inferior prognosis documented for MM patients with high Mel-1 expression at initial diagnosis (Wuilleme-Toumi, Robillard et al. 2005). Given our results linking GLUT4 activity with the maintenance of Mcl-1 expression, it stands to reason that the reduction in Mcl-1 expression noted by Ikezoe et al. during ritonavir treatment results from glucose transport inhibition. Therefore, ritonavir treatment represents a novel therapeutic approach to indirectly target Mcl-1 expression.

We have also uncovered universal overexpression of GLUT8 and GLUT11 in human myeloma cell lines in comparison to normal B lymphocytes. The expression of these isoforms in normal human tissues is even more limited than that of GLUT4. GLUT8 mRNA is highly abundant only in spermatocytes and is present at relatively low levels in muscle and spleen tissues (Doege, Schumann et al. 2000; Augustin, Riley et al. 2005). This transporter is thought to be involved in a glucose transport process associated with an as yet unidentified intracellular organelle (Scheepers, Doege et al. 2001). GLUT11 mRNA is most abundant in brain and skeletal and cardiac muscle tissues (Doege, Bocianski et al. 2001). GLUT11 protein predominantly localizes to the plasma membrane, the result of a translocation process that may occur constitutively given the fact that serum starvation does not result in intracellular sequestration when expressed ectopically in COS-7 cells (Scheepers, Schmidt et al. 2005). Despite the lack of understanding surrounding the normal physiological and cancer-associated functions of GLUT8 and GLUT11, we propose that these proteins may represent attractive therapeutic targets in myeloma given their restricted expression in normal tissues. Drug discovery efforts aimed at these GLUT family members may not only yield effective drugs but will also facilitate discovery of their unique functionalities and relevance to myeloma pathobiology.

The development of small molecule inhibitors to the SGLT2 protein, functionally related to the GLUT family, is a significant step towards demonstrating the feasibility of targeting transporter- and tissue-specific glucose entry (Li, Zhang et al. 2011)). The SGLT2 transporter is responsible for re-absorption of glucose in the kidney and inhibition of this specific transporter has been shown to improve circulating plasma glucose levels by enhanced excretion of glucose (Li, Zhang et al. 2011). This advancement underscores the feasibility of targeting glucose-transporter specific glucose utilization for the treatment of cancer as outlined by our studies.

Our laboratory has worked extensively on defining the mechanism of action of purine analogues 8-amino-adenosine (8-NH2-Ado) and 8-chloro-adenosine (Gandhi, Ayres et al. 2001; Krett, Davies et al. 2004; Ghias, Ma et al. 2005). In our recent publication (Shanmugam, McBrayer et al. 2009) we report that 8-$NH_2$-Ado targets cellular metabolism by inducing a rapid decline in glucose consumption, the magnitude of which correlates with toxicity in various myeloma cell lines. FIG. 1A demonstrates a rapid decline in glucose consumption in the sensitive MM.1S cells after 5 hrs of 3 uM 8-NH2-Ado treatment.

Results and Discussion

8-Amino-Adenosine Treatment Causes Translocation of GLUT4 in MM.1S cells.

To explore mechanisms underlying the decrease in glucose consumption elicited by 8-$NH_2$-Ado in the MM.1S cell line, we examined the regulation of glucose transporters that regulate the primary rate limiting step in glycolysis (Rodriguez-Enriquez, Marin-Hernandez et al. 2009). We examined expression and subcellular localization of GLUT1 and GLUT4, two highly expressed glucose transporters in B lymphocytes. Despite a 40% decline in glucose consumption rates within the first five hours of treatment (FIG. 1A), no substantial changes in GLUT1 or GLUT4 expression levels are observed at this time (FIG. 1B). The expression of both GLUT1 and 4 are diminished by 24 hours, potentially contributing to the further decline in glucose transport rates seen between 5 and 17 hours. Since the activity of these proteins depends upon insertion into the plasma membrane, we next evaluated subcellular distribution by immunofluorescence confocal microscopy (FIG. 1C). Untreated MM.1S cells show a homogenous cytoplasmic and plasma membrane distribution of GLUT1 and 4. Both cells exhibit some cytoplasmic GLUT4 staining which increases at the periphery of the cell, indicating basal plasma membrane localization. Treatment of MM.1S cells with 8-$NH_2$-Ado reduces this basal cell surface localization of GLUT4 and causes selective aggregation of GLUT4 within the trans-golgi network as evidenced by co-localization with anti-golgin 97 (Shanmugam, McBrayer et al. 2009). The temporal association between GLUT4 intracellular aggregation and the decline in glucose transport rate in MM.1S cells yields two observations: 1) GLUT1 likely accounts for less than 60% of the overall glucose consumption of MM.1S cells and 2) GLUT4 may occupy a major role in this process in myeloma.

Figure 2:
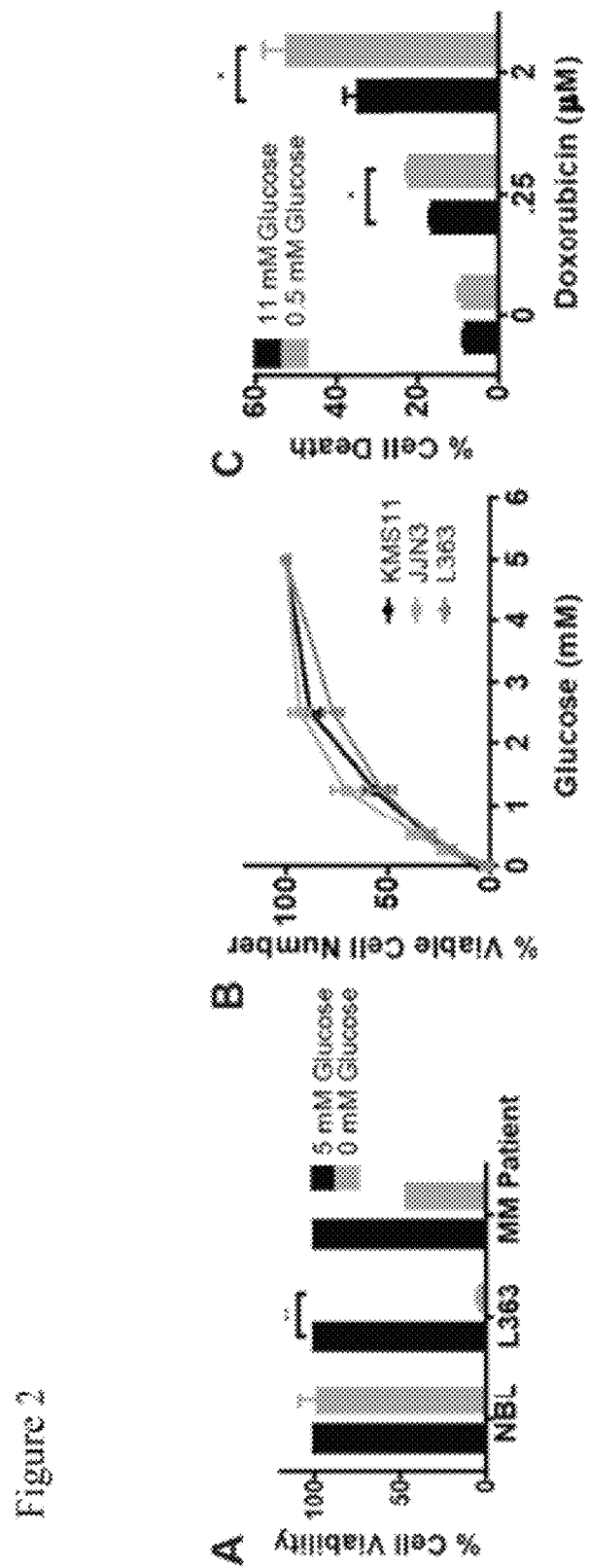
FIG. 2 shows that myeloma cells exhibit increased glucose dependency which sustains growth, viability, and chemoresistance. (A) Primary normal B lymphocytes and CD138+ cells isolated from an MM patient and L363 cells were cultured in medium containing 0 or 5 mM glucose for 48 (NBL, L363) or 72 (MM Patient) hours. Cell viability was determined by flow cytometric analysis of AnnexinV/DAPI staining and normalized to 5 mM samples. Data are means±SEM (n=2). (B) Indicated cells were cultured as in (A) with various concentrations of glucose for 72 hours. Viable cell quantities were determined by MTS assay and normalized to 5 mM samples. Data are means±SEM. (C) U266 myeloma cells were cultured in 11 or 0.5 mM glucose-containing medium for 48 hours in the presence of the indicated concentrations of doxorubicin. Cell death was determined by flow cytometric analysis of DAPI staining. Data are means±SEM. *p<0.05 **p<0.01.

Glucose Deprivation Attenuates Proliferation, Viability and Chemoresistance of Myeloma Cells. To independently ascertain the contribution of glucose in maintaining myeloma cell proliferation and survival we cultured L363 myeloma cells, normal B lymphocytes (NBL), and primary MM cells in medium containing either a physiological glucose concentration (5 mM) or medium devoid of glucose and assessed the impact on cellular viability (FIG. 2 A). Under these conditions, greater than 95% of L363 cells and 50% of the primary MM cells undergo apoptosis while the viability of normal cells is not impacted. Stepwise reductions in glucose concentrations elicit effects ranging from mild growth inhibition to cell death across the three genotypically distinct'myeloma cell lines (FIG. 2 B). This stark contrast with B lymphocytes indicates the myeloma cells are uniquely susceptible to glucose deprivation. To address whether an increase in glucose utilization is associated with chemoresistance that characterizes late stage MM, we tested whether the refractory U266 cell line could be sensitized to doxorubicin by sub-lethal culture in 0.5 mM glucose medium (FIG. 2C). Indeed, U266 cells display significantly greater sensitivity to doxorubicin under glucose-limiting conditions. To identify the GLUT family member(s) responsible for increased glucose consumption rates, we undertook an unbiased real-time qRT- PCR-based screen to identify GLUT isoforms with elevated expression in MM cell lines as compared to normal B lymphocytes.

Figure 3:
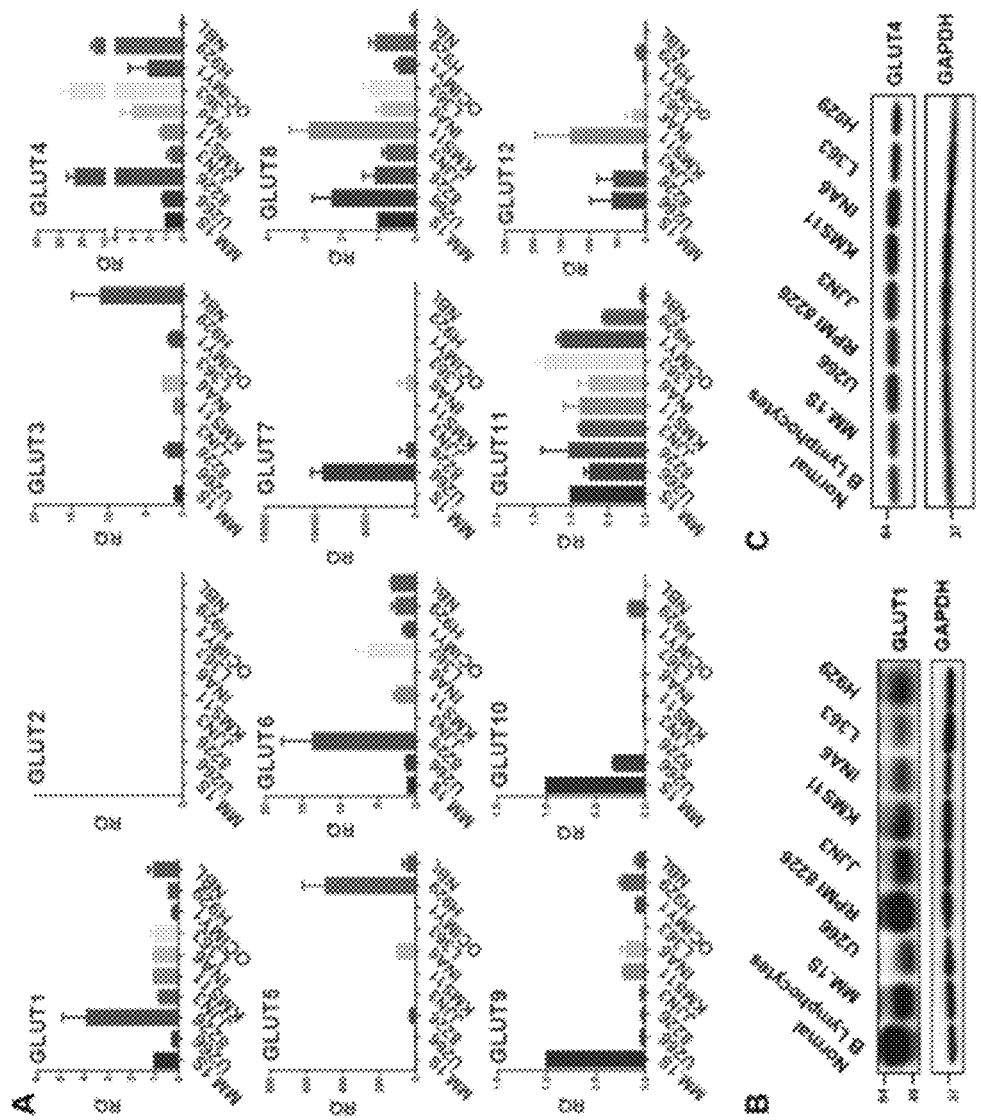
FIG. 3 shows that PCR-based screen of glucose transporter gene expression profiles reveals increased GLUT4, GLUT8 and GLUT11 mRNA abundance across all myeloma cell lines compared to normal B lymphocytes with validation of GLUT8 and GLUT11 expression levels from patient sample gene expression analyses. (A) Nine myeloma cell lines and normal B lymphocytes (NBL, rightmost bars) isolated from three healthy donors were analyzed for expression of GLUTs 1-12 by quantitative real time RT-PCR. Relative quantification (RQ) of the expression of each gene is displayed and normalized to the MM.1S cell line. Data are means±SEM. For GLUT4, GLUT8, and GLUT11, comparisons between each MM cell line and normal B lymphocytes exhibit one-tailed p values <0.05 with the exception of GLUT4 expression in the OCIMYI cell line. (B-C) Immunoblot analysis of GLUT1 and GLUT4 expression across NBL and myeloma cell lines. Representative blots are shown.

Glucose Transporter qRT-PCR Analysis in a Panel of Myeloma Cell Lines Demonstrates mRNA Transcript Up-Regulation of a Subset of Glucose Transporters in Comparison to Normal B Cells. We selected 9 myeloma cell lines and purified CD19+ normal B lymphocytes from peripheral blood mononuclear cells isolated from healthy donors to determine relative expression levels of GLUT family members. The data generated is from 3 experimental repeats including B cells from three different donors and is normalized internally using 3 loading controls (YWHAZ, RPL13A, EIF4A2). These loading controls were identified to have relatively uniform expression across the myeloma cell lines and normal 13 cells and were used to generate a normalization factor utilizing geNorm™ software. Relative quantification values were then normalized to the expression of the MM.1S cell line. Through this analysis we identified up-regulation of GLUTs 4, 8, 11 and 12 in several cell lines (at least 5) and in a lesser number of cell lines up-regulation of GLUT1, 5, 9 and 10 (FIG. 3 A). Transporters up-regulated across multiple cell lines could have more therapeutic potential and were therefore selected for further study. Interestingly, GLUT3, which is important for glucose transport in normal B cells, is significantly down-regulated in all cell lines tested. GLUT4 is thought to be insulin-regulated and GLUT8 and GLUT11 share uniquely high affinities for glucose.

Immunoblot Analysis Demonstrating Expression of GLUTs 1 and 4 in Myeloma Cell Lines Compared to Normal B Cells, Thus Supporting qRT-PCR Data. Representative immunoblots of GLUT1 and GLUT4 are shown in FIG. 3 B-C. Interestingly, we do not detect overexpression of GLUT1 at the protein level, thought to be responsible for enhanced glucose uptake in solid tumor cells (Macheda, Rogers et al. 2005).

Patient Gene Array Expression Analysis Validates Glut Gene Family Expression Pattern Determined by qRT-PCR Analysis of Myeloma Cell Lines. To validate the clinical significance of our qRT-PCR analysis of GLUT expression in myeloma cell lines we analyzed microarray gene expression studies of MM patient sample data available through the Oncomine™ database (Oncomine™). While myeloma is a highly heterogeneous plasma cell dyscrasia we were able to validate the decrease in GLUT3 expression and over-expression of GLUT8 and GLUT11 in several studies (Table 1).

TABLE 1

Microarray analyses of myeloma patient samples confirm downregulation of GLUT3 and upregulation of GLUT8 and GLUT11

| Isoform | Study title* | Probeset ID | Fold change | P value[†] | Samples compared[‡] |
|---|---|---|---|---|---|
| GLUT3 | Zhan Myeloma | M20681_at | −3.219 | 2.13E−10 | MM (74) vs Normal PCs from Tonsil (7) and Bone Marrow (37) |
| GLUT3 | Zhan Myeloma 3 | 202498_s_at | −2.36 | 3.00E−03 | Smoldering MM (12) vs Normal PCs from Bone Marrow (22) |
| GLUT3 | Zhan Myeloma 3 | 202499_s_at | −2.125 | 0.015 | Smoldering MM (12) vs Normal PCs from Bone Marrow (22) |
| GLUT8 | Zhan Myeloma 3 | 239426_at | 1.382 | 0.05 | Smoldering MM (12) vs Normal PCs from Bone Marrow (22) |
| GLUT11 | Mattioli Myeloma | 221262_s_at | 1.855 | 3.00E−03 | MM (39) vs MGUS (7) and Plasma Cell Leukemia (6) |
| GLUT11 | Mulligan Myeloma | 221262_s_at | 1.565 | 5.95E−03 | MM Patients: Dexamethasone Non-Responders (42) vs Responders (28) |
| GLUT1 | Zhan Myeloma 3 | 201250_s_at | 1.858 | 5.87E−04 | Smoldering MM (12) vs Normal PCs from Bone Marrow (22) |
| GLUT1 | Zhan Myeloma 3 | 201249_at | −1.000 | 0.5 | Smoldering MM (12) vs Normal PCs from Bone Marrow (22) |

*Oncomine ™ (Compendia Bioscience, Ann Arbor, MI) was used for analysis and visualization.
[†]P values listed are from Oncomine ™ where possible or represent results of one-tailed, unpaired t tests between two clinical groups where values are not available.
[‡]Numbers in parentheses represent number of samples in each clinical group.
MM indicates multiple myeloma;
PCs, plasma cells; and
MGUS, monoclonal gammopathy of undetermined significance.

The GLUT8 and GLUT11 patient data that match our in vitro results are particularly important, as the patient samples reflect gene expression patterns in the context of the typical hypoxic myeloma microenvironment. In addition, the patient gene-expression studies provide no evidence of GLUT1 overexpression in myeloma.

Figure 4:
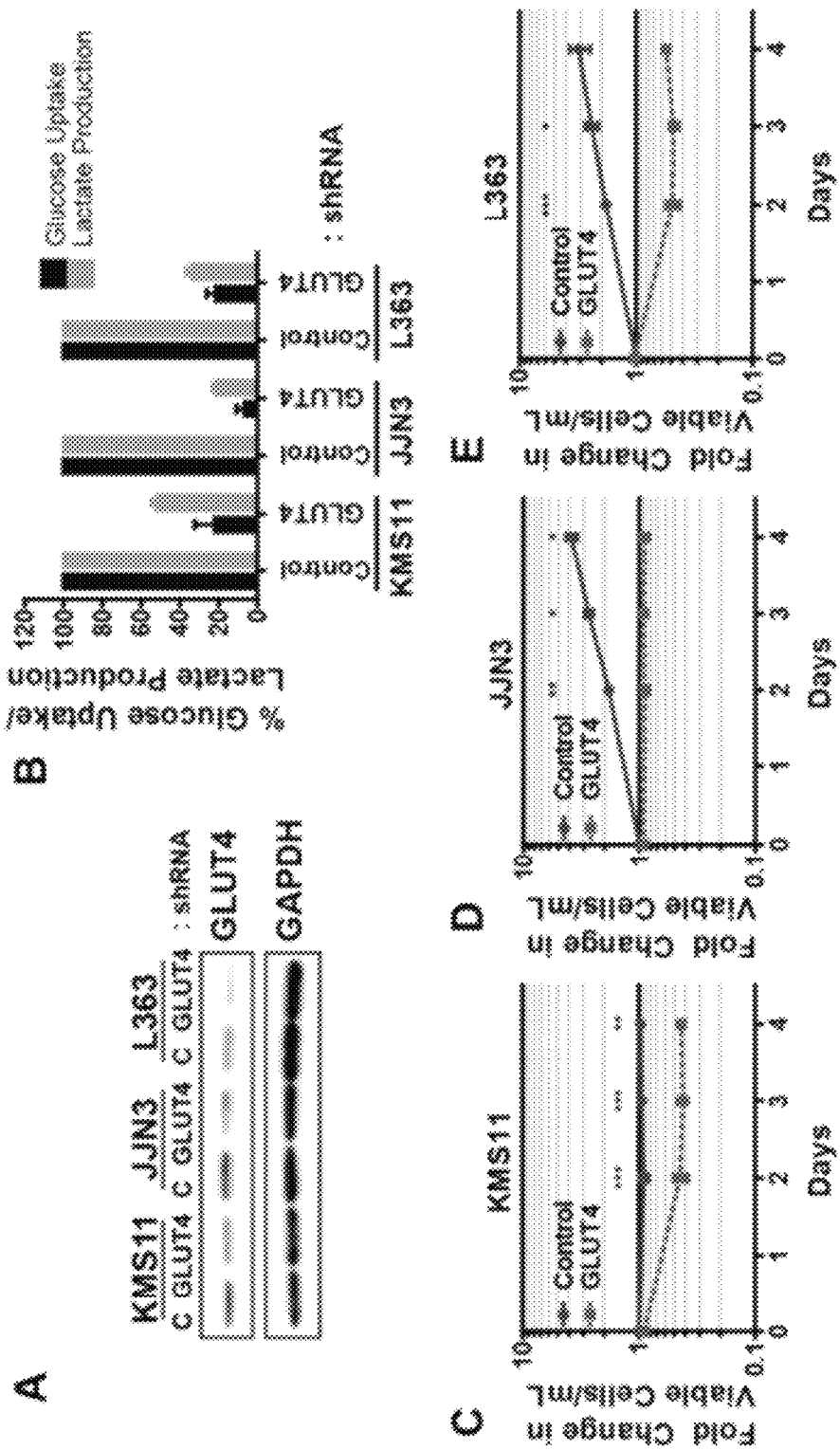
FIG. 4 shows that expression of constitutively plasma membrane-localized GLUT4 is necessary for glucose consumption, lactate production, growth and viability of myeloma cells. (A) Cells were transduced with control (C), non-targeted shRNA or GLUT4-targeted shRNA and incubated 3 (L363) or 4 (JJN3, KMS11) days before protein extraction and analysis of GLUT4 protein expression was performed. Representative blot is shown. (B) Cells from part A were cultured in 5 mM glucose-containing medium for 5 hours. Glucose consumption rates and lactate production rates were determined and normalized to control shRNA-expressing cells. (C-E) Cells from part A were analyzed for viability and proliferation. Viable cells densities are expressed as fold change relative to the day 0 reading of control shRNA-expressing cells. (F) GLUT4 localization in CD138+ primary myeloma cells, myeloma cell lines and normal B lymphocytes was assessed via confocal immunofluorescence microscopy. Arrows indicate regions of cell surface GLUT4 immunoreactivity. Black boxes highlight normal controls. Representative images are shown (n=1 for all primary samples). (G) KMS11 cells, L363 cells and normal PBMC were lysed for extraction of plasma membrane-associated proteins or total cellular protein content. GLUT4 immunoblot analysis was performed on the resulting fractions. Na+/K+ATPase and GAPDH serve as loading controls. (H) Densitometric quantification of band intensities in part G normalized first to corresponding loading controls and subsequently to KMS11 cells. Data in parts B-E and H are means±SEM. With exception noted in part F, for data in parts A-H n≥3. *P <0.05 P<0.01*P<0.005.
Figure 4:
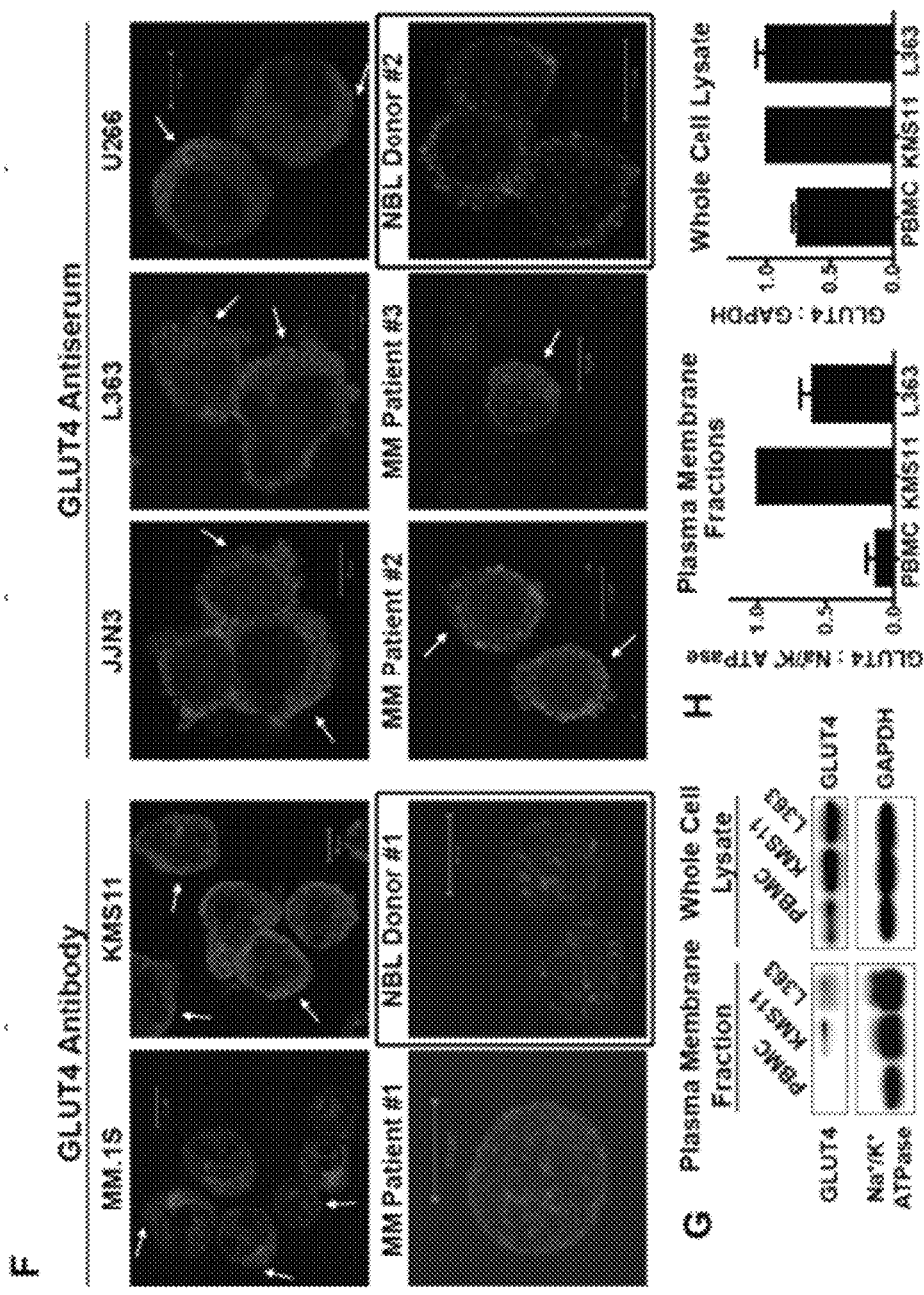

GLUT4 Activity Maintains Glucose Consumption, Growth and Viability in Myeloma. Transduction of three MM cell lines with a GLUT4-targeted shRNA resulted in potent suppression of GLUT4 expression, glucose consumption, and lactate production, suggesting that GLUT4 activity is critical for maintaining glycolytic flux (FIG. 4, A and B). These effects were associated with cytotoxic outcomes in KMS11 and L363 cells and complete cytostasis in JJN3 cells (FIG. 4 C-E). Furthermore, these results recapitulate the impact of low glucose culture on these cell lines; only JJN3 cells are resistant to apoptosis during short-term glucose starvation (data not shown).

MM Cell Lines and Patient Samples Exhibit Basal Plasma Membrane Localization of GLUT4. In insulin-responsive normal tissues, GLUT4 is rendered inactive under basal conditions via retention in cytoplasmic storage vesicles. Upon insulin stimulation, these vesicles translocate to and fuse with the plasma membrane, thus activating GLUT4 (Hon and Pessin 2007). We reasoned that the basal dependence of MM cells on this transporter may be due to an atypical, constitutive translocation of GLUT4 to the cell surface, expanding on our observations in the MM.1S and U266 cell lines. We used confocal immunofluorescence microscopy to determine the subcellular distribution of GLUT4 (FIG. 4 F). Analysis of five different MM cell lines, normal B cells from 2 two healthy donors, and primary CD138+ cells from three myeloma patients reveals a myeloma-specific distribution of GLUT4 to the plasma membrane. In contrast, the GLUT4 pool in normal B lymphocytes appears to reside in an exclusively intracellular compartment, consistent with the canonical paradigm of GLUT4 regulation. Subcellular fractionation to isolate plasma membrane-associated proteins of peripheral blood mononuclear cells (PBMC) from healthy donors and MM cells provided quantitative verification of differential GLUT4 localization (FIG. 4 G). While GLUT4 levels in whole cell lysates are only marginally increased in the MM lines, the plasma membrane-associated GLUT4 content in myeloma is significantly increased over the virtually undetectable level in PBMC (FIG. 4 H). These data suggest elevated rates of glucose uptake in myeloma are achieved through the disengagement of GLUT4 intracellular retention mechanisms, resulting in the partial constitutive activation of GLUT4.

Figure 5:
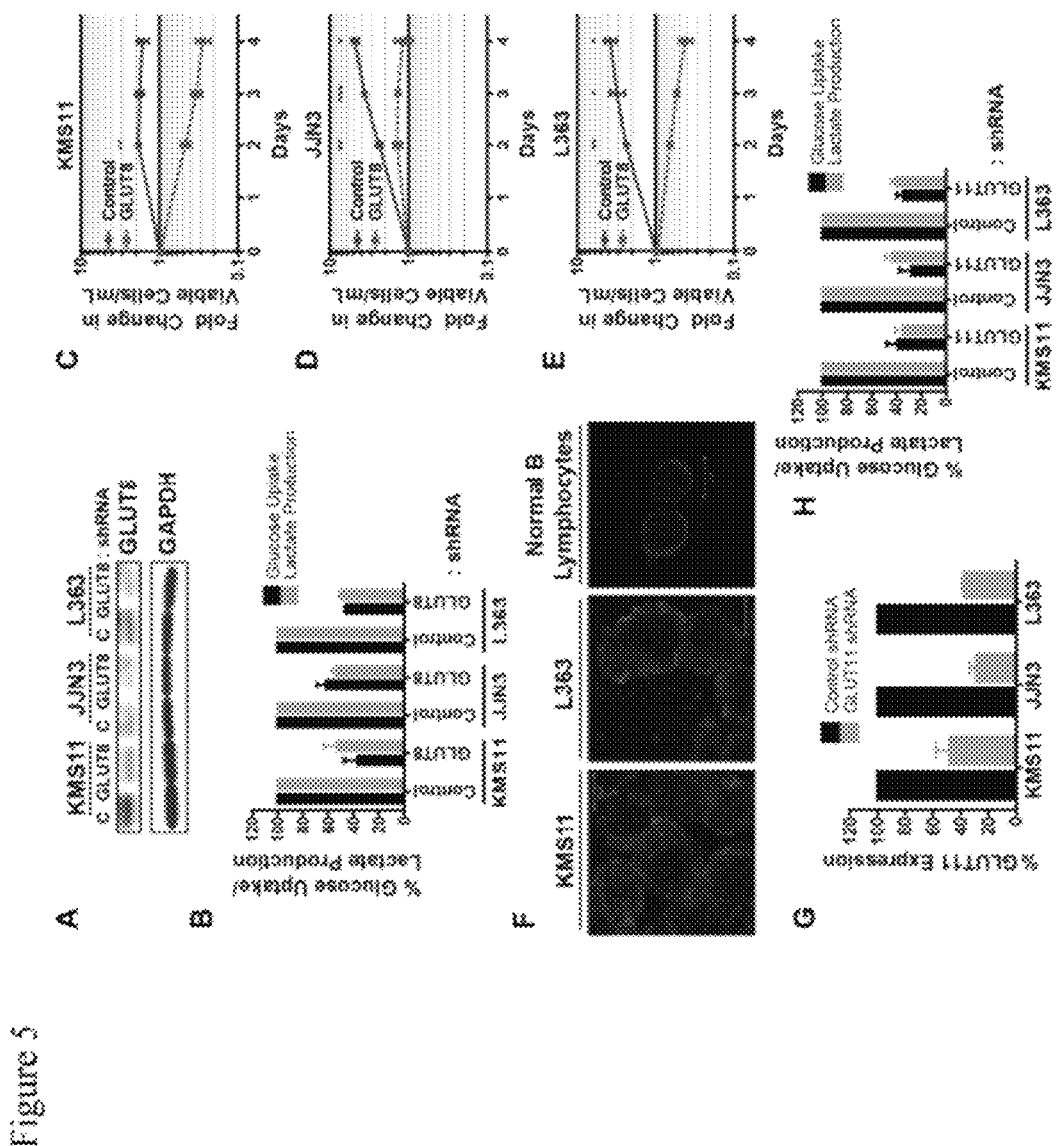
FIG. 5 shows that RNAi-mediated suppression of GLUT8 or GLUT11 compromises the viability of myeloma cell lines. (A) Cells were transduced with the indicated shRNAs and incubated 2 days before protein extraction. Representative blot is shown. (B) Cells from part A were cultured in 5 mM glucose-containing medium for 5 hours. Glucose consumption rates and lactate production rates were determined and normalized to control shRNA-expressing cells. (C-E) Cells from part A were analyzed for viability and proliferation. Viable cell densities are expressed as fold change relative to the day 0 reading of control shRNA-expressing cells. (F) GLUT8 subcellular localization in KMS11 cells, L363 cells and normal B lymphocytes was assessed via confocal immunofluorescence microscopy. Representative images are shown. (G) Cells were transduced with the indicated shRNAs and incubated 3 days before RNA extraction. (H) Cells from part G were cultured in 5 mM glucose-containing medium for 5 hours. Glucose consumption rates and lactate production rates were determined and normalized to control shRNA-expressing cells. (I-K) Cells from part G were analyzed for viability and proliferation. Viable cell densities are expressed as fold change relative to the day 0 reading of control shRNA-expressing cells. (L) GLUT11 subcellular localization in KMS11 cells, L363 cells and normal B lymphocytes was assessed via confocal immunofluorescence microscopy. Background, non-specific staining with pre-immune serum is included as a control. Representative images are shown. Data in parts B-E and G-K are means±SEM. For data in parts A-L, n≥3. *P<0.05P<0.01*P<0.005.
Figure 5:
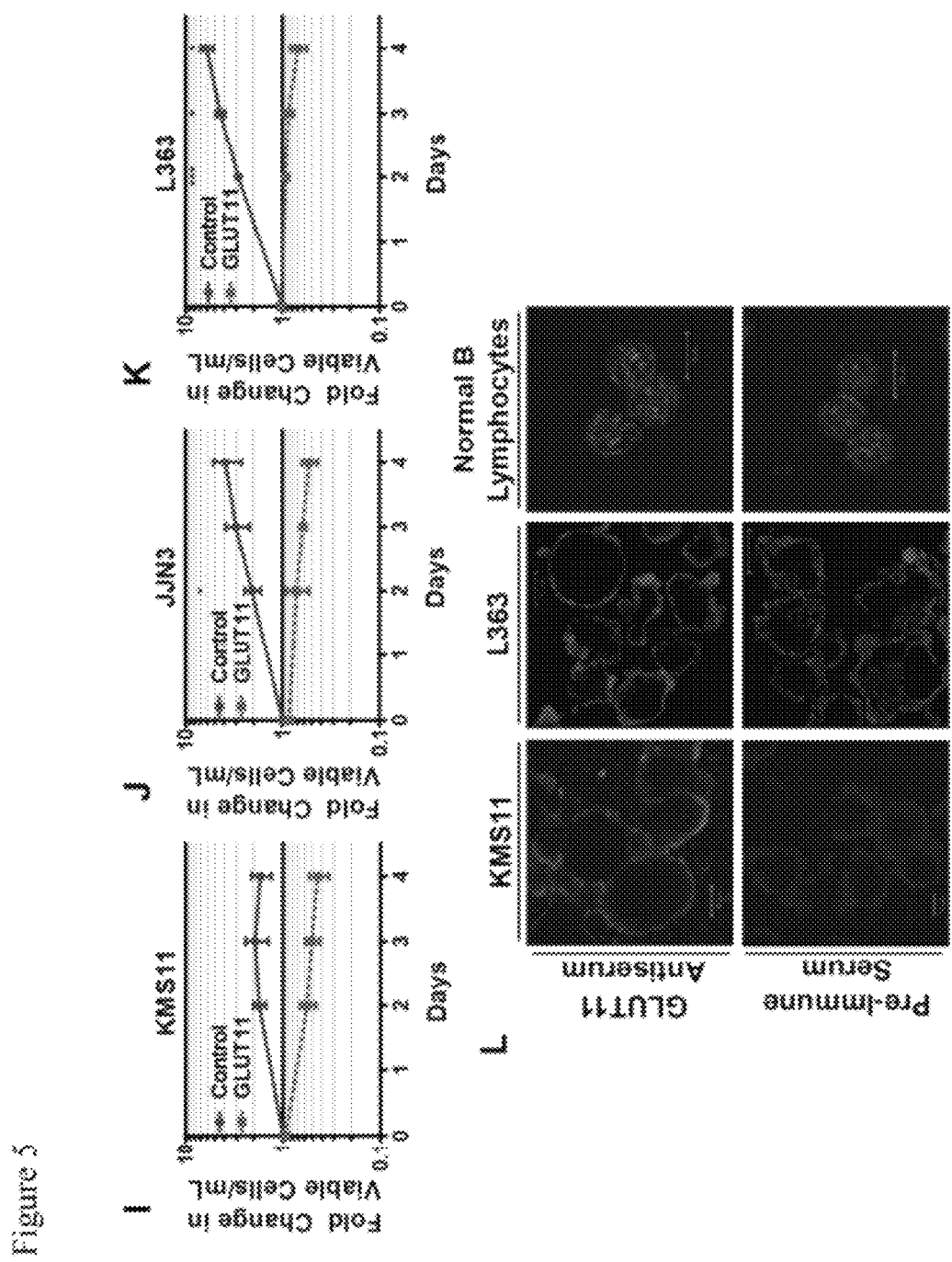

GLUT8 and GLUT11 Activities are Essential but Ambiguous in MM Cells. Knockdown of GLUT8 (FIG. 5 A) resulted in robust cell death induction in KMS11 and L363 cells as well as growth inhibition and a delayed decline in viability in the JJN3 background (FIG. 5 C-E) despite modest effects on glucose transport and lactate production rates (FIG. 5 B). The specificity of the GLUT8 shRNA used was validated by comparison with a second, less efficient shRNA (data not shown). In addition to the minor impact on glucose consumption, the punctate, exclusively cytoplasmic GLUT8 staining pattern in both myeloma cells and B lymphocytes (FIG. 5 F) supports a hypothetical role for GLUT8 distinct from that of GLUT1 or GLUT4. This intracellular distribution is incompatible with a primary function of GLUT8 in whole-cell glucose supply. Indeed, both our own immunofluorescence data (FIG. 5 F) and that from other groups (Piroli, Grillo et al. 2002; Widmer, Uldry et al. 2005) indicate that the primary function of GLUT8 may be in organellar glucose transport. Regardless of function, the substantial impact of GLUT8 inhibition on myeloma growth and viability suggests that this transporter may be a promising therapeutic target worthy of additional investigation.

Finally, we performed similar analyses to address the unique contribution of GLUT11. Knockdown of GLUT11 results in moderate downregulation of glucose consumption and lactate extrusion rates (FIGS. 5 G and H). We observed a range of apoptotic effects, ranging from severe (KMS11) to mild (L363) (FIG. 5 I-K). In all cases, cells did not proliferate without endogenous GLUT11 activity. Specificity of the RNAi approach is confirmed by an association between the knockdown efficiency of two distinct GLUT11-targeted shRNAs and ensuing cell death (data not shown). Our immunofluorescence studies confirm that GLUT11 overexpression in myeloma extends from transcript to protein; the marked differential signal intensity observed at the plasma membrane in KMS11 and L363 cells stained with pre-immune serum and GLUT11 antiserum is not seen in the control B lymphocytes (FIG. 5 L). With regards to the putative function of GLUT11 in myeloma, it is noteworthy that GLUT11 silencing in JJN3 cells results in less potent suppression of glucose consumption rates but much greater cell death induction relative to GLUT4 knockdown. This phenotypic discordance intimates that the functional capabilities of GLUT11 may not completely be encompassed by the glucose transport activity attributed to this protein.

Figure 6:
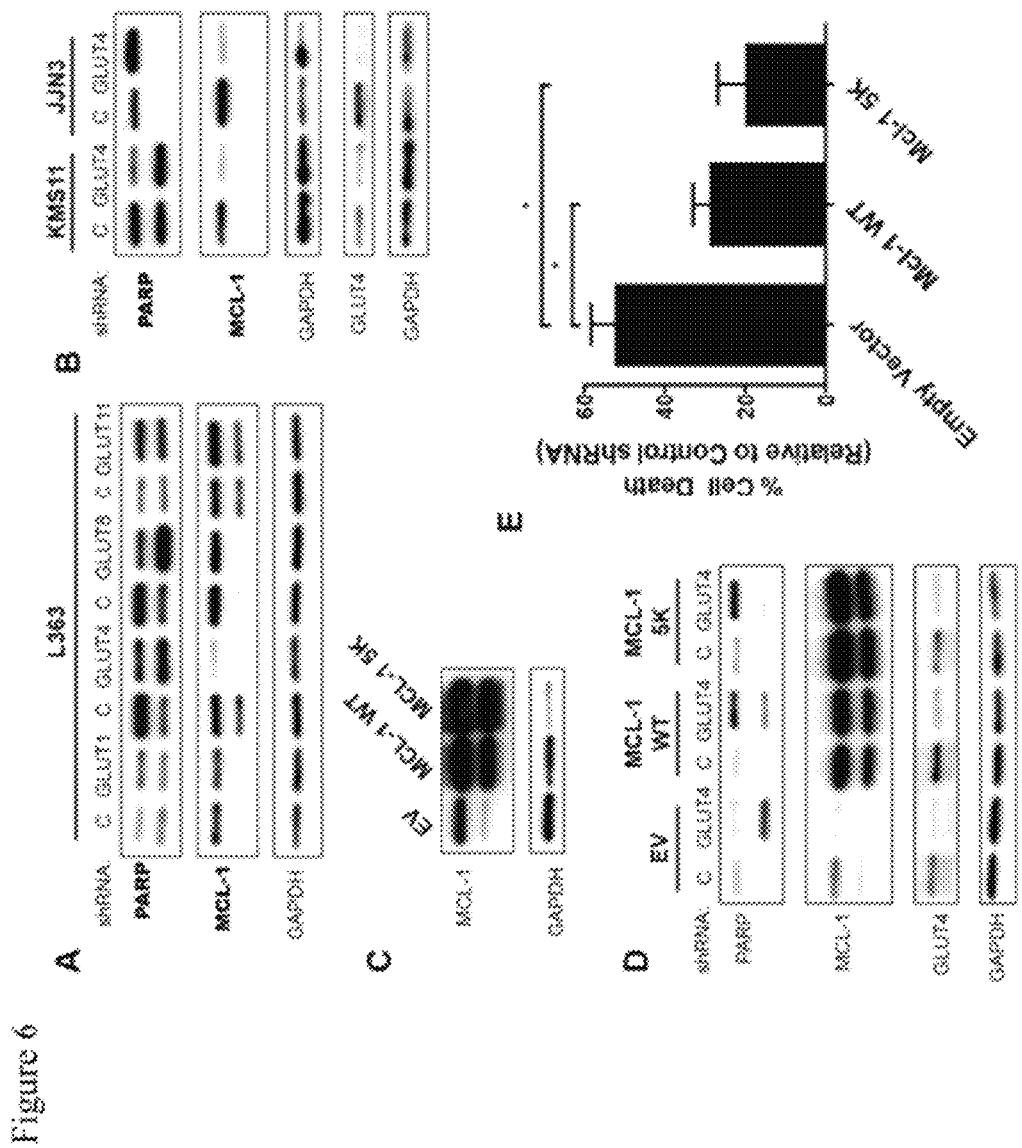
FIG. 6 shows that cytotoxicity of GLUT4 silencing is mediated by Mcl-1 suppression. (A) L363 cells were transduced with the indicated shRNAs and cell lysates were prepared after achieving greater than 70% knockdown. Representative blots indicating PARP and MCL-1 expression are shown. (B) KMS11 and JJN3 cells were transduced with control (C) or GLUT4-targeted shRNA and incubated for 4 days before lysate preparation. Representative blots for PARP, MCL-1 and GLUT4 are shown. (C) L363 cells were transduced with an empty vector control (EV), wild type MCL1 (Mcl-1 WT), or ubiquitination-resistant MCL1 mutant (Mcl-1 5K). Stable cell lines were generated and Mcl-1 expression was assessed by immunoblot analysis. Representative blot is shown. (D) L363 stable cell lines from part C were transduced with control- or GLUT4 targeted shRNA and incubated for three days before immunoblot analysis of GLUT4, Mcl-1 and PARP. Representative blot is shown. (E) Cells from part D were subjected to flow cytometric viability analysis via AnnexinV/DAPI staining. Data is normalized to control shRNA-expressing cells within each cell line. Data in part E are means±SEM. For data in parts A-E, n≥3. *P<0.05 P<0.01 *P<0.005.

GLUT4 Inhibition Suppresses Mcl-1 Expression. From the previous observations we conclude that GLUT4 is the principal family member supporting increased glucose consumption rates in myeloma. To elucidate the pathway connecting GLUT4 activity with maintenance of cell survival, we performed immunoblot analysis of key glucose-regulated and apoptosis-related proteins in lysates from L363 cells expressing control, GLUT1, GLUT4, GLUT8 and GLUT11 shRNAs (FIG. 6 A). Importantly, PARP cleavage correlates tightly with the extent of cell death induced by the knockdown of each GLUT isoform (FIGS. 4 E and 5 E and K). In L363, KMS11 and JJN3 cells, GLUT4 expression is specifically associated with the maintenance of Mcl-1 expression (FIG. 6 B). The pathway linking glucose metabolism with Mcl-1 stabilization has been described previously in the context of non-transformed hematopoietic progenitor cells; in this case, growth factor deprivation-induced inhibition of glucose metabolism results in GSK-3-mediated phosphorylation and ubiquitination-dependent degradation of Mcl-1 (Zhao, Altman et al. 2007). This in addition to the fact that MCL-1 is a key modulator of apoptosis led us to hypothesize that Mcl-1 reduction was critical for GLUT4 knockdown-mediated cell death in myeloma cells. To test this hypothesis, we generated L363 stable cell lines expressing an empty vector (EV), a wild type MCL-1 cDNA (MCL-1 WT), or an MCL-1 mutant cDNA encoding a degradation-resistant protein lacking five lysine residues necessary for ubiquitination (MCL-1 5K) (Snyder, Shroff et al. 2009) (FIG. 6 C). Upon transduction of these lines with GLUT4 shRNA, we note decreases in PARP cleavage corresponding to the extent of cell death reversal (FIGS. 6 D and E). The cytoprotection afforded by the two MCL-1 constructs correlates with Mcl-1 protein abundance, with nearly complete reversal of cytotoxicity achieved through expression of the MCL-1 5K mutant. The ability to substantially reduce Mcl-1 expression through GLUT4 inhibition can have profound clinical implications. Previous studies have demonstrated inferior prognosis for MM patients with high Mcl-1 expression at initial diagnosis (Wuilleme-Toumi, Robillard et al. 2005).

Figure 7:
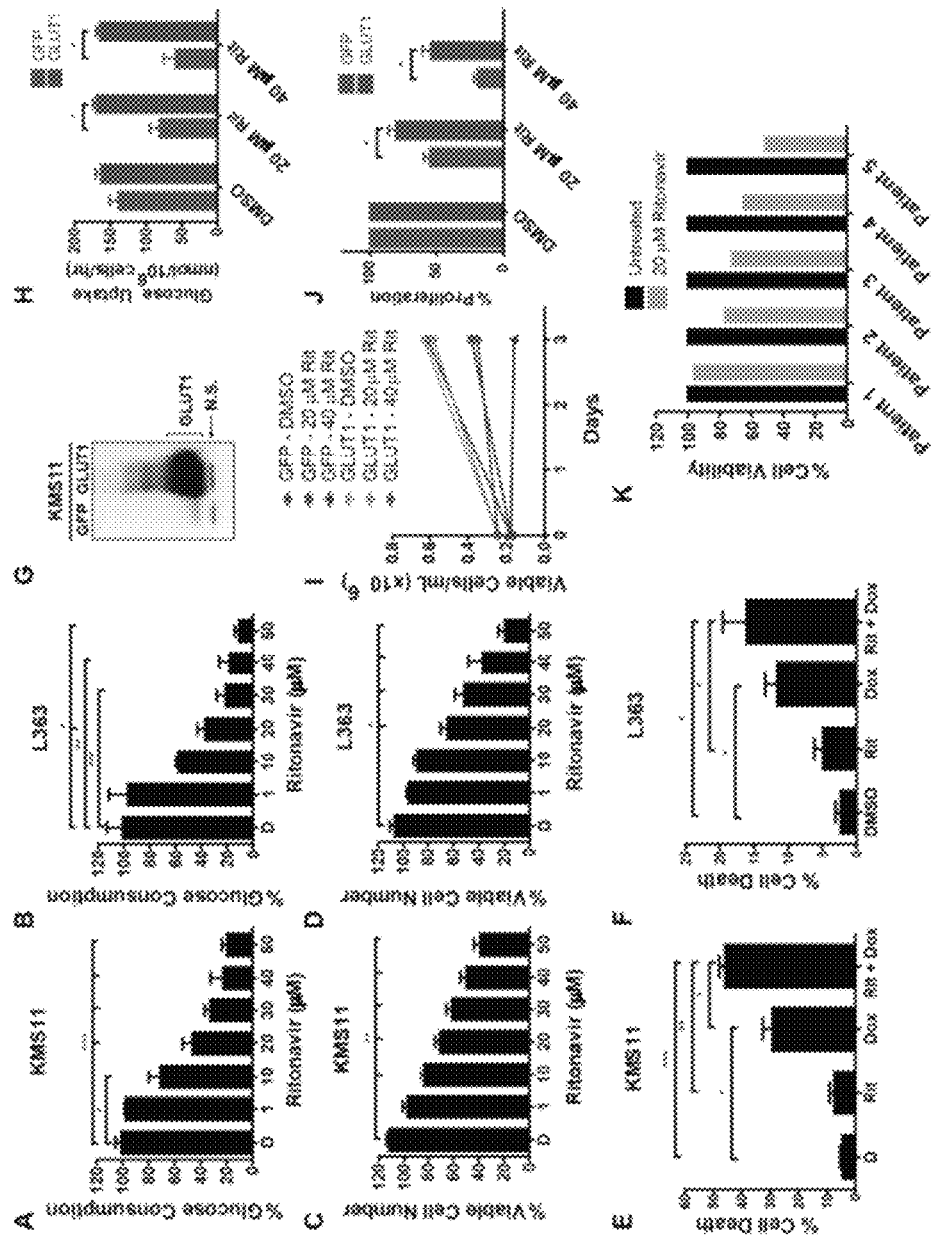
FIG. 7 shows that GLUT4-specific glucose transport inhibition elicited by the HIV therapeutic monavir suppresses myeloma growth and viability in addition to chemosensitizing cells to doxorubicin. (A) KMS11 and (B) L363 cells were plated in 5 mM glucose medium with ritonavir or DMSO (D) for 17 hours. Glucose consumption rates are normalized to untreated cells (not shown). (C) KMS11 and (D) L363 cells were treated with ritonavir or DMSO for 12 hours. Relative viable cell numbers were determined by MTS assay and normalized to untreated cells (not shown). (E) KMS11 and (F) L363 cells were treated with 20 μM ritonavir with or without 0.075 (KMS11) and 0.025 μM (L363) doxorubicin or the combination for 72 hrs and cellular viability assessed by AnnexinV/DAPI staining. (G) Stable KMS11 cell lines were generated expressing empty vector or GLUT1 and GLUT1 levels were assessed by immunoblot. Representative blot is shown. N.S. indicates non-specific band. (H) Stable cell lines from part G were treated with DMSO or ritonavir (Rit) for 5 hours and glucose consumption was assessed. (1) Cell proliferation was measured in the stable cell lines described in part G treated with ritonavir (Rit) or DMSO for 72 hours. A representative experiment is shown. (J) Cell proliferation rates from multiple experiments represented by part G are normalized to DMSO-treated cells. (K) Primary myeloma cells were treated with DMSO or ritonavir for 72 hours before AnnexinV/DAPI staining. Values are normalized to DMSO-treated samples (n=1 for each patient sample). Data are means±SEM with n≥3. *P<0.05 P<0.01 *P<0.005.

Exploiting the GLUT4-Inhibitory Properties of the HIV Therapeutic Ritonavir Suppresses Myeloma Growth. Lastly, based on the significant impact of GLUT4 knockdown on myeloma cell proliferation we decided to test the efficacy of a class of HIV protease inhibitors that has been demonstrated to specifically inhibit GLUT4 (Murata, Hruz et al. 2000). Serendipitously, certain HIV protease inhibitors elicit off-target inhibitory effects on GLUT4 which are both specific and direct (Murata, Hruz et al. 2000; Murata, Hruz et al. 2002; Kalla Vyas, Koster et al. 2010). We have determined that the most potent member of this drug class, ritonavir, yields therapeutically desirable effects against myeloma cells in vitro. As shown in FIG. 7 A-D, ritonavir treatment yields dose-dependent abrogation of both glucose transport and proliferation in KMS11 and L363 cells. Additionally, ritonavir treatment recapitulates the doxorubicin-sensitizing effects of glucose limitation shown in FIG. 2C (FIG. 7 E-F). To assess the contribution of glucose transport inhibition to ritonavir-induced cell growth arrest, we generated KMS11 stable cell lines expressing SLC2AI (GLUT1) or GFP (FIG. 7G). Given the specificity of ritonavir for GLUT4, GLUT1 expression completely mitigated ritonavir-induced glucose transport inhibition and simultaneously conferred robust resistance to prolonged treatment (FIG. 7 H-J). This effect overcomes a noticeably reduced growth rate exhibited by the GLUT1-overexpressing line (FIG. 7I). To determine the clinical applicability of these findings, we tested ritonavir for cytotoxicity towards primary myeloma cells. In FIG. 7K, a range of cell death induction is seen in patient samples following incubation with a concentration of ritonavir (20 µM) which is approximately equivalent to the peak plasma level routinely achieved in humans (Hsu, Granneman et al. 1997). The off-target effects of the FDA approved drug ritonavir on GLUT4

(Murata, Hruz et al. 2002; Noor, Seneviratne et al. 2002) are proof of principle that patients can tolerate drugs targeting GLUT4 that lead to impaired glucose uptake and hyperglycemia in chronic, high dose regimens. However, if these compounds were given in conjunction with chemotherapy cycles, anti-tumor efficacy may be greatly potentiated while off-target effects may be reduced due to shorter durations of administration. Importantly, these metabolic symptoms associated with PI administration have been demonstrated to be reversible and subside over time following treatment termination. In summation, we have provided data on the abnormal expression of a subset of glucose transporters in myeloma, highlighting a crucial role for GLUT4. We believe therapeutic targeting of GLUT4 in myeloma with ritonavir or indinavir may have beneficial chemosensitization effects as well as activity as stand-alone agents in the context of the hypoxic and/or hypoglycemic myelomatous bone marrow microenvironment.

References

All publications, patent applications, patents and other references mentioned herein are expressly incorporated by reference in their entirety, to the same extent as if each were incorporated by reference individually. In case of conflict, the present specification, including definitions, will control.

Airley, R., J. Loncaster, et al. (2001). "Glucose transporter glut-1 expression correlates with tumor hypoxia and predicts metastasis-free survival in advanced carcinoma of the cervix." *Clin Cancer Res* 7(4): 928-934.

Augustin, Riley, et al. (2005). "GLUT8 contains a [DE]XXXL[LI] sorting motif and localizes to a late endosomal/lysosomal compartment." *Traffic* 6(12): 1196-1212.

Bartel, T. B., J. Haessler, et al. (2009). "F18-fluorodeoxyglucose positron emission tomography in the context of other imaging techniques and prognostic factors in multiple myeloma." *Blood* 114(10): 2068-2076.

Berruti, A., R. Bitossi, et al. (2002). "Time to progression in metastatic breast cancer patients treated with epirubicin is not improved by the addition of either cisplatin or lonidamine: final results of a phase III study with a factorial design." *J Clin Oncol* 20(20): 4150-4159.

Bredella, M. A., L. Steinbach, et al. (2005). "Value of FDG PET in the assessment of patients with multiple myeloma." *AJR Am J Roentgenol* 184(4): 1199-1204.

Castellani, M., M. Carletto, et al. (2010). "The prognostic value of F-18 fluorodeoxyglucose bone marrow uptake in patients with recent diagnosis of multiple myeloma: a comparative study with Tc-99m sestamibi." *Clin Nucl Med* 35(1): 1-5.

Chow, W. A., C. Jiang, et al. (2009). "Anti-HIV drugs for cancer therapeutics: back to the future?" *Lancet Oncol* 10(1): 61-71.

Cooper, R., S. Sarioglu, et al. (2003). "Glucose transporter-(GLUT-1): a potential marker of prognosis in rectal carcinoma?" *Br J Cancer* 89(5): 870-876.

Dewan, M. Z., J. N. Uchihara, et al. (2006). "Efficient intervention of growth and infiltration of primary adult T-cell leukemia cells by an HIV protease inhibitor, ritonavir." *Blood* 107(2): 716-724.

Doege, H., A. Bocianski, et al. (2001). "Characterization of human glucose transporter (GLUT) 11 (encoded by SLC2A11), a novel sugar-transport facilitator specifically expressed in heart and skeletal muscle." *Biochem J* 359(Pt 2): 443-449.

Doege, H., A. Schumann, et al. (2000). "GLUT8, a novel member of the sugar transport facilitator family with glucose transport activity." *J Biol Chem* 275(21): 16275-16280.

Durie, B. G., A. D. Waxman, et al. (2002). "Whole-body (18)F-FDG PET identifies high-risk myeloma." *J Nucl Med* 43(11): 1457-1463.

Gandhi, V., M. Ayres, et al. (2001). "8-chloro-cAMP and 8-chloro-adenosine act by the same mechanism in multiple myeloma cells." *Cancer Res* 61(14): 5474-5479.

Ghias, K., C. Ma, et al. (2005). "8-Amino-adenosine induces loss of phosphorylation of p38 mitogen-activated protein kinase, extracellular signal-regulated kinase 1/2, and Akt kinase: role in induction of apoptosis in multiple myeloma." *Mol Cancer Ther* 4(4): 569-577.

Gills, J. J., J. Lopiccolo, et al. (2007). "Nelfinavir, A lead HIV protease inhibitor, is a broad-spectrum, anticancer agent that induces endoplasmic reticulum stress, autophagy, and apoptosis in vitro and in vivo." *Clin Cancer Res* 13(17): 5183-5194.

Goldman, N. A., E. B. Katz, et al. (2006). "GLUT1 and GLUT8 in endometrium and endometrial adenocarcinoma." *Mod Pathol* 19(11): 1429-1436.

Gupta, A. K., G. J. Cerniglia, et al. (2005). "HIV protease inhibitors block Akt signaling and radiosensitize tumor cells both in vitro and in vivo." *Cancer Res* 65(18): 8256-8265.

Hertel, J., H. Struthers, et al. (2004). "A structural basis for the acute effects of HIV protease inhibitors on GLUT4 intrinsic activity." *J Biol Chem* 279(53): 55147-55152.

Hou, J. C. and J. E. Pessin (2007). "Ins (endocytosis) and outs (exocytosis) of GLUT4 trafficking." *Curr Opin Cell Biol* 19(4): 466-473.

Hsu, A., G. R. Granneman, et al. (1997). "Multiple-dose pharmacokinetics of ritonavir in human immunodeficiency virus-infected subjects." *Antimicrob Agents Chemother* 41(5): 898-905.

Ikezoe, T., T. Saito, et al. (2004). "HIV-1 protease inhibitor induces growth arrest and apoptosis of human multiple myeloma cells via inactivation of signal transducer and activator of transcription 3 and extracellular signal-regulated kinase 1/2." *Mol Cancer Ther* 3(4): 473-479.

Jin, S., R. S. DiPaola, et al. (2007). "Metabolic catastrophe as a means to cancer cell death." *J Cell Sci* 120(Pt 3): 379-383.

Kalla Vyas, A., J. C. Koster, et al. (2010). "Effects of the HIV protease inhibitor ritonavir in GLUT4 knockout mice." *J Biol Chem*.

Ko, Y. H., B. L. Smith, et al. (2004). "Advanced cancers: eradication in all cases using 3-bromopyruvate therapy to deplete ATP." *Biochem Biophys Res Commun* 324(1): 269-275.

Koster; J. C., M. S. Remedi, et al. (2003). "HIV protease inhibitors acutely impair glucose-stimulated insulin release." *Diabetes* 52(7): 1695-1700.

Krett, N. L., K. M. Davies, et al. (2004). "8-amino-adenosine is a potential therapeutic agent for multiple myeloma." *Mol Cancer Ther* 3(11): 1411-1420.

Kumar, S., C. S. Bryant, et al. (2009). "Ritonavir blocks AKT signaling, activates apoptosis and inhibits migration and invasion in ovarian cancer cells." *Mol Cancer* 8: 26.

Li, A. R., J. Zhang, et al. (2011). "Discovery of non-glucoside SGLT2 inhibitors." *Bioorg Med Chem Lett* 21(8): 2472-2475.

Macheda, M. L., S. Rogers, et al. (2005). "Molecular and cellular regulation of glucose transporter (GLUT) proteins in cancer." *J Cell Physiol* 202(3): 654-662.

Manolescu, A. R., K. Witkowska, et al. (2007). "Facilitated hexose transporters: new perspectives on form and function." *Physiology (Bethesda)* 22: 234-240.

Maratou, E., G. Dimitriadis, et al. (2007). "Glucose transporter expression on the plasma membrane of resting and activated white blood cells." *Eur J Clin Invest* 37(4): 282-290.

Maschek, G., N. Savaraj, et al. (2004). "2-deoxy-D-glucose increases the efficacy of adriamycin and paclitaxel in human osteosarcoma and non-small cell lung cancers in vivo." *Cancer Res* 64(1): 31-34.

Murata, H., P. W. Hruz, et al. (2000). "The mechanism of insulin resistance caused by HIV protease inhibitor therapy." *J Biol Chem* 275(27): 20251-20254.

Murata, H., P. W. Hruz, et al. (2002). "Indinavir inhibits the glucose transporter iso form Glut4 at physiologic concentrations." *AIDS* 16(6): 859-863.

Noor, M. A., T. Seneviratne, et al. (2002). "Indinavir acutely inhibits insulin-stimulated glucose disposal in humans: a randomized, placebo-controlled study." *AIDS* 16(5): F1-8.

Oncomine™, Compendia Bioscience, Ann Arbor, Mich.

Pedersen, P. L., S. Mathupala, et al. (2002). "Mitochondrial bound type II hexokinase: a key player in the growth and survival of many cancers and an ideal prospect for therapeutic intervention." *Biochim Biophys Acta* 1555(1-3): 14-20.

Pelicano, H., D. S. Martin, et al. (2006). "Glycolysis inhibition for anticancer treatment." *Oncogene* 25(34): 4633-4646.

Piroli, G. G., C. A. Grillo, et al. (2002). "Peripheral glucose administration stimulates the translocation of GLUT8 glucose transporter to the endoplasmic reticulum in the rat hippocampus." *J Comp Neurol* 452(2): 103-114.

Raez L E, L. V., Papadopoulus K, et al. (2006). "Phase I trial of glycolitic inhibition with 2-deoxyglucose and docetaxel for patients with solid tumors." *AACR Meet Abstract.*

Ramanathan, A. and S. L. Schreiber (2009). "Direct control of mitochondrial function by mTOR." *Proc Natl Acad Sci USA* 106(52): 22229-22232.

Rodriguez-Enriquez, S., A. Marin-Hernandez, et al. (2009). "Kinetics of transport and phosphorylation of glucose in cancer cells." *J Cell Physiol* 221(3): 552-559.

Rudich, A., D. Konrad, et al. (2003). "Indinavir uncovers different contributions of GLUT4 and GLUT1 towards glucose uptake in muscle and fat cells and tissues." *Diabetologia* 46(5): 649-658.

Scheepers, A., H. Doege, et al. (2001). "Mouse GLUT8: genomic organization and regulation of expression in 3T3-L1 adipocytes by glucose." *Biochem Biophys Res Commun* 288 (4): 969-974.

Scheepers, A., S. Schmidt, et al. (2005). "Characterization of the human SLC2A11 (GLUT11) gene: alternative promoter usage, function, expression, and subcellular distribution of three isoforms, and lack of mouse orthologue." *Mol Membr Biol* 22(4): 339-351.

Shanmugam, M., S. K. McBrayer, et al. (2009). "Targeting glucose consumption and autophagy in myeloma with the novel nucleoside analogue 8-aminoadenosine." *J Biol Chem* 284(39): 26816-26830.

Snyder, C. M., E. H. Shroff, et al. (2009). "Nitric oxide induces cell death by regulating anti-apoptotic BCL-2 family members." *PLoS One* 4(9): e7059.

Srirangam, A., R. Mitra, et al. (2006). "Effects of HIV protease inhibitor ritonavir on Akt-regulated cell proliferation in breast cancer." *Clin Cancer Res* 12(6): 1883-1896.

Widmer, M., M. Uldry, et al. (2005). "GLUT8 subcellular localization and absence of translocation to the plasma membrane in PC12 cells and hippocampal neurons." *Endocrinology* 146(11): 4727-4736.

Wuilleme-Toumi, S., N. Robillard, et al. (2005). "Mcl-1 is overexpressed in multiple myeloma and associated with relapse and shorter survival." *Leukemia* 19(7): 1248-1252.

Xu, R. H., H. Pelicano, et al. (2005). "Synergistic effect of targeting mTOR by rapamycin and depleting ATP by inhibition of glycolysis in lymphoma and leukemia cells." *Leukemia* 19(12): 2153-2158.

Xu, R. H., H. Pelicano, et al. (2005). "Inhibition of glycolysis in cancer cells: a novel strategy to overcome drug resistance associated with mitochondrial respiratory defect and hypoxia." *Cancer Res* 65(2): 613-621.

Zamora-Leon, S. P., D. W. Golde, et al. (1996). "Expression of the fructose transporter GLUT5 in human breast cancer." *Proc Natl Acad Sci USA* 93(5): 1847-1852.

Zhao, Y., B. J. Altman, et al. (2007). "Glycogen synthase kinase 3alpha and 3beta mediate a glucose-sensitive antiapoptotic signaling pathway to stabilize Mcl-1." *Mol Cell Biol* 27(12): 4328-4339.

Zhong, D., L. Xiong, et al. (2009). "The glycolytic inhibitor 2-deoxyglucose activates multiple prosurvival pathways through IGF1R." *J Biol Chem* 284(35): 23225-23233.

Zong, W. X., D. Ditsworth, et al. (2004). "Alkylating DNA damage stimulates a regulated form of necrotic cell death." *Genes Dev* 18(11): 1272f-1282.

We claim:

1. A method of treating multiple myeloma in a patient having multiple myeloma, the method comprising:
    (a) administering, a GLUT4 inhibitor to the patient, wherein the GLUT4 inhibitor inhibits glucose transport by GLUT4 and wherein the GLUT4 inhibitor is ritonavir; and (b) administering a DNA damaging agent to the patient, wherein the DNA damaging agent is doxorubicin.

2. The method of claim 1, wherein the GLUT4 inhibitor is administered after the patient has fasted for at least 4 hours.

\* \* \* \* \*